(12) United States Patent
Konrad

(10) Patent No.: US 7,521,022 B2
(45) Date of Patent: Apr. 21, 2009

(54) RECEIVING DEVICE COMPRISING AN ADJUSTABLE COVERING ELEMENT

(75) Inventor: Franz Konrad, Oberndorf bei Schwanenstadt (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 850 days.

(21) Appl. No.: 10/530,301

(22) PCT Filed: Sep. 29, 2003

(86) PCT No.: PCT/AT03/00287

§ 371 (c)(1),
(2), (4) Date: Apr. 4, 2005

(87) PCT Pub. No.: WO2004/030539

PCT Pub. Date: Apr. 15, 2004

(65) Prior Publication Data

US 2005/0288607 A1    Dec. 29, 2005

(30) Foreign Application Priority Data

Oct. 2, 2002   (AT) ............................. A 1492/2002
Mar. 30, 2003  (AT) ............................. A 842/2003

(51) Int. Cl.
*A61B 5/00* (2006.01)
(52) U.S. Cl. .................. 422/103; 604/110; 604/164.12; 600/573; 600/576; 600/577
(58) Field of Classification Search ................. 422/102; 604/110, 164.12; 600/573, 576, 577
See application file for complete search history.

(56) References Cited

U.S. PATENT DOCUMENTS 4,774,964 A * 10/1988 Bonaldo ..................... 600/576

(Continued)

FOREIGN PATENT DOCUMENTS

WO      WO 92/20281 A    11/1992

(Continued)

OTHER PUBLICATIONS

International Search Report.

*Primary Examiner*—Jill Warden
*Assistant Examiner*—Bryan T Kilpatrick
(74) *Attorney, Agent, or Firm*—Collard & Roe, P.C.

(57) ABSTRACT

The invention relates to a holding device (1) with a holding container (2) for a holding vessel, in particular a blood sample collecting tube, in which the holding container (2) surrounds a holding chamber (7) with a container wall (6), and in the direction of a longitudinal axis (8) comprises a proximal and a distal end (9, 10) spaced part from one another, with a needle holder (4) for a needle arrangement (14) that can be attached thereto, with a first adjusting device (15) for the needle holder (4) and with a cover element (3) for the needle arrangement (14) mountable on the needle holder (4) in the disposal position of the needle holder (4). The cover element (3) is arranged in the position of use of the needle holder (4) adjacent thereto on the side furthest from the proximal end (9) in the holding chamber (7) and is arranged with an if necessary releasable locking device (16) between the cover element (3) and the holding container (2) in the position of use relative to the latter, whereby between the needle holder (4) and the cover element (3) a further adjusting device (17) is arranged.

69 Claims, 12 Drawing Sheets

U.S. PATENT DOCUMENTS

| | | | |
|---|---|---|---|
| 5,407,436 A | 4/1995 | Toft et al. | |
| 5,423,758 A | 6/1995 | Shaw | |
| 5,769,826 A | 6/1998 | Johnson et al. | |
| 5,810,775 A | 9/1998 | Shaw | |
| 6,524,276 B1 * | 2/2003 | Halseth et al. | 604/110 |
| 7,182,734 B2 * | 2/2007 | Saulenas et al. | 600/573 |
| 7,258,678 B2 * | 8/2007 | Wilkinson | 604/110 |
| 2002/0099355 A1 | 7/2002 | Chen | |
| 2003/0105432 A1 * | 6/2003 | Halseth et al. | 604/164.12 |

FOREIGN PATENT DOCUMENTS

| | | |
|---|---|---|
| WO | WO 9220281 | 11/1992 |
| WO | WO 93/23098 | 11/1993 |
| WO | WO 95/16389 | 6/1995 |
| WO | WO 98/41249 | 9/1998 |
| WO | WO 99/23947 A | 5/1999 |
| WO | WO 9923947 | 5/1999 |
| WO | WO 01/93924 A1 | 12/2001 |
| WO | WO 0193924 | 12/2001 |

* cited by examiner

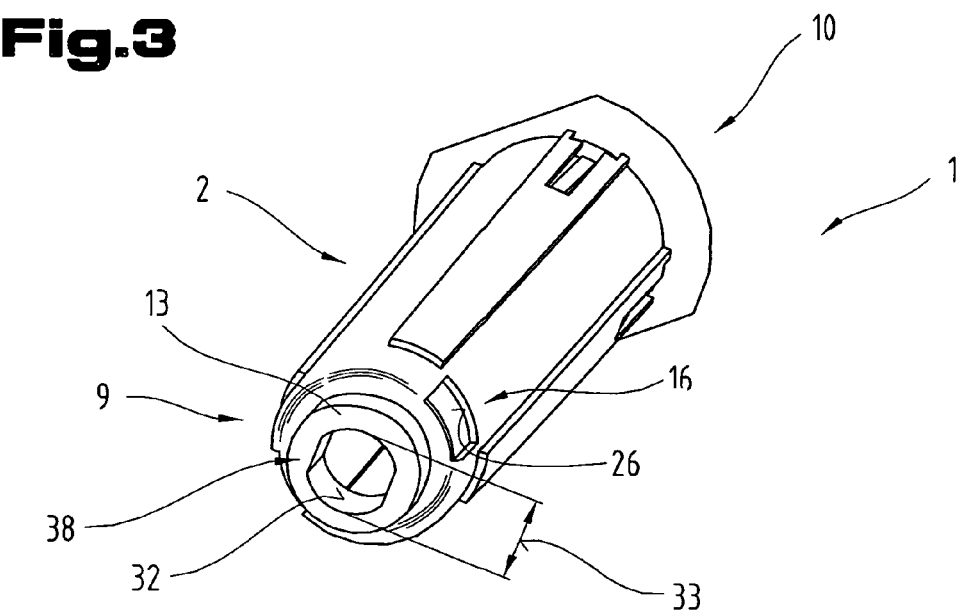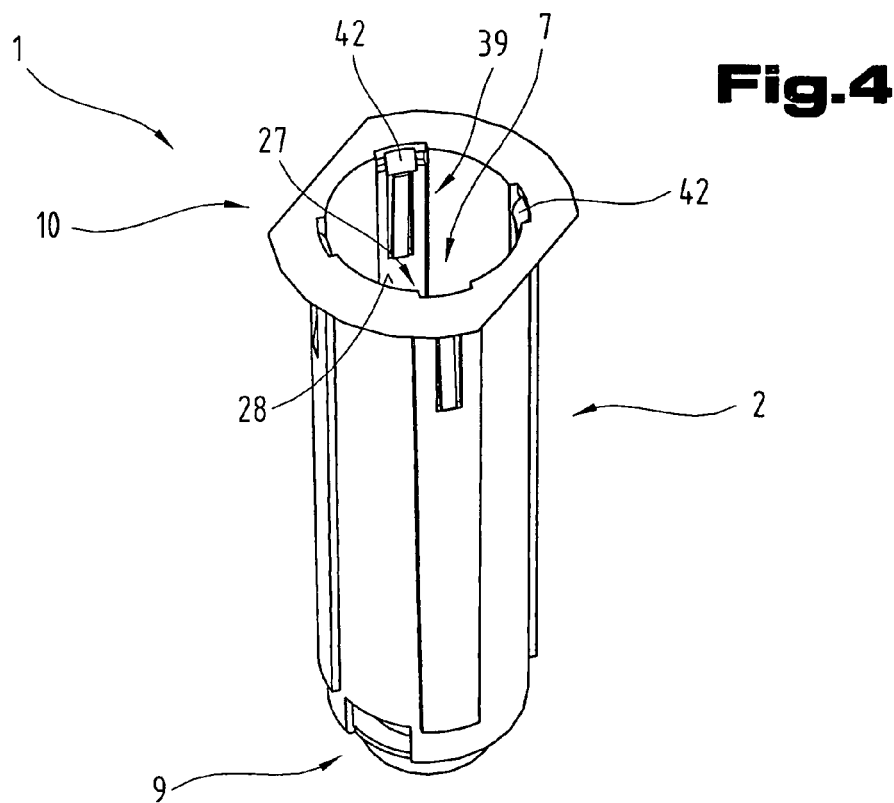

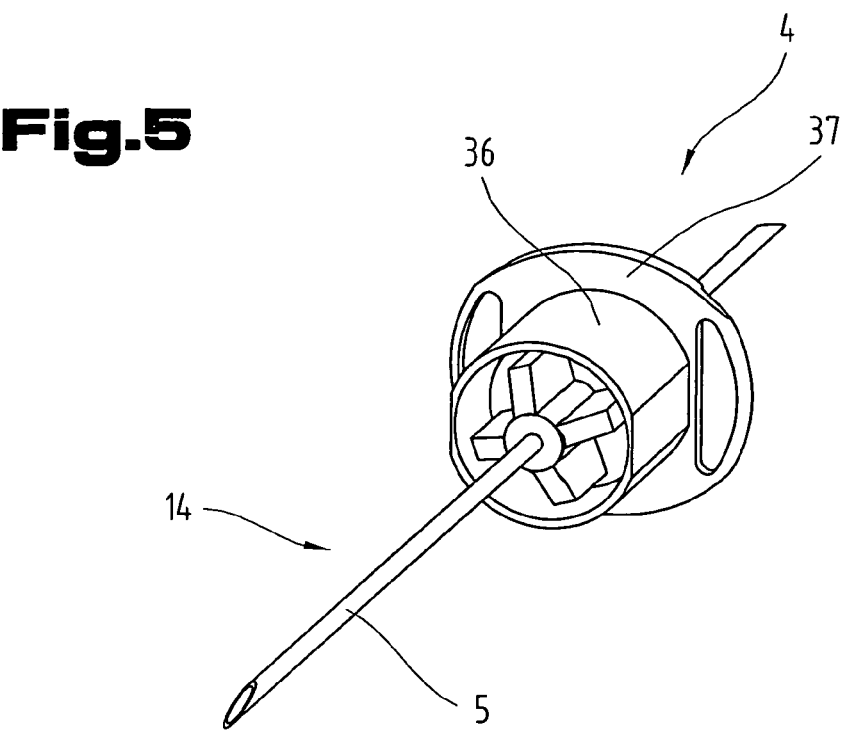
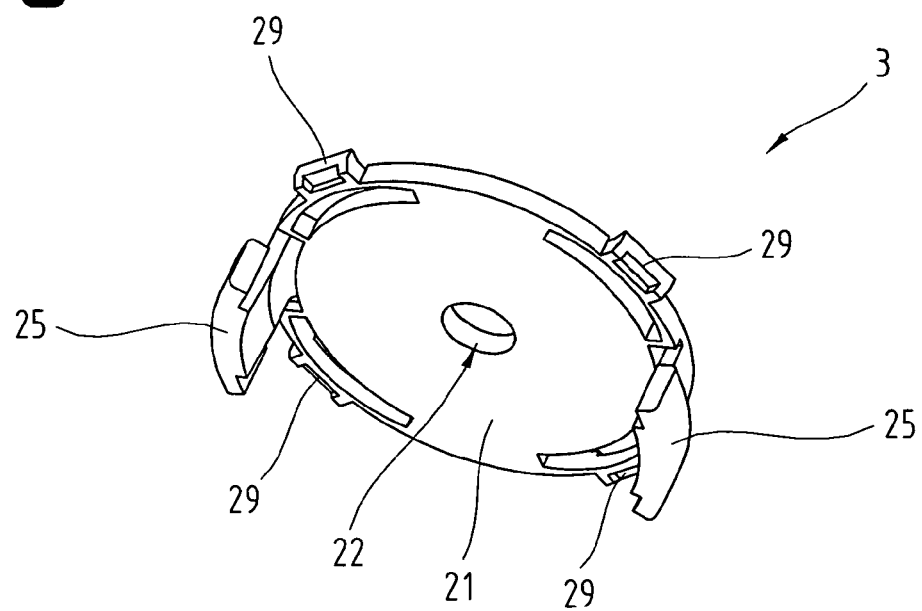

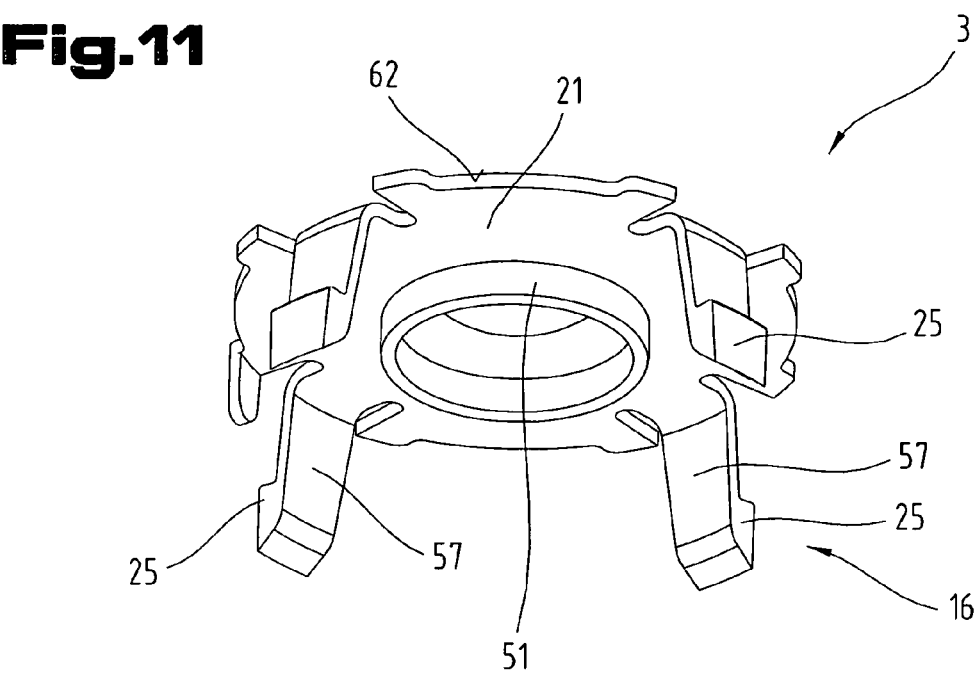
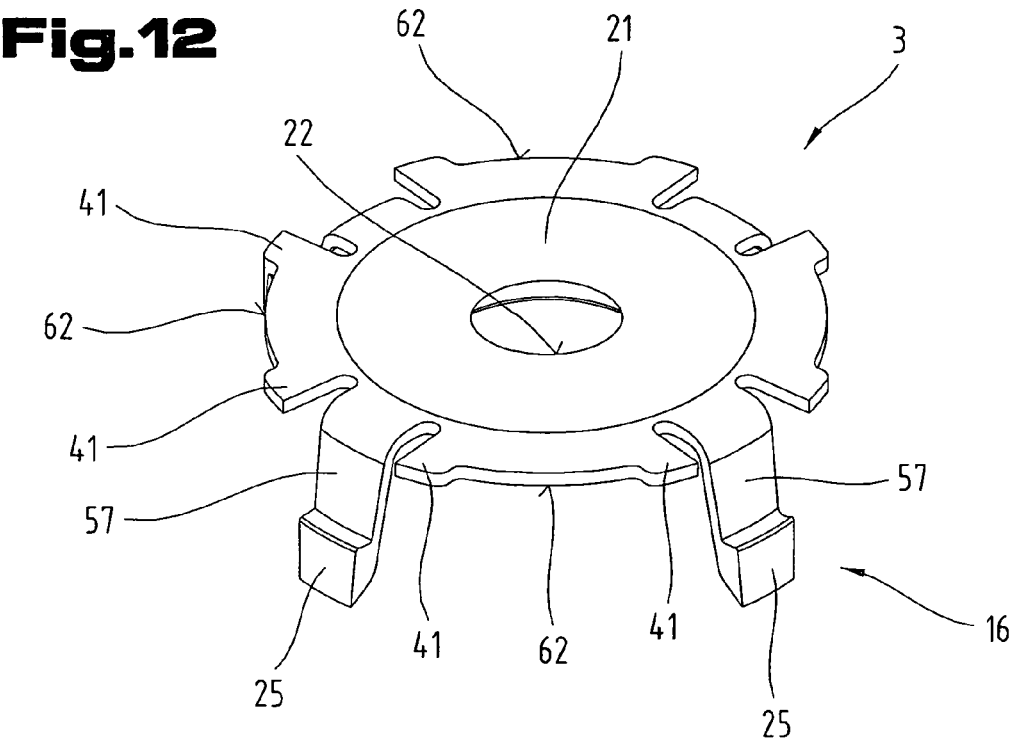

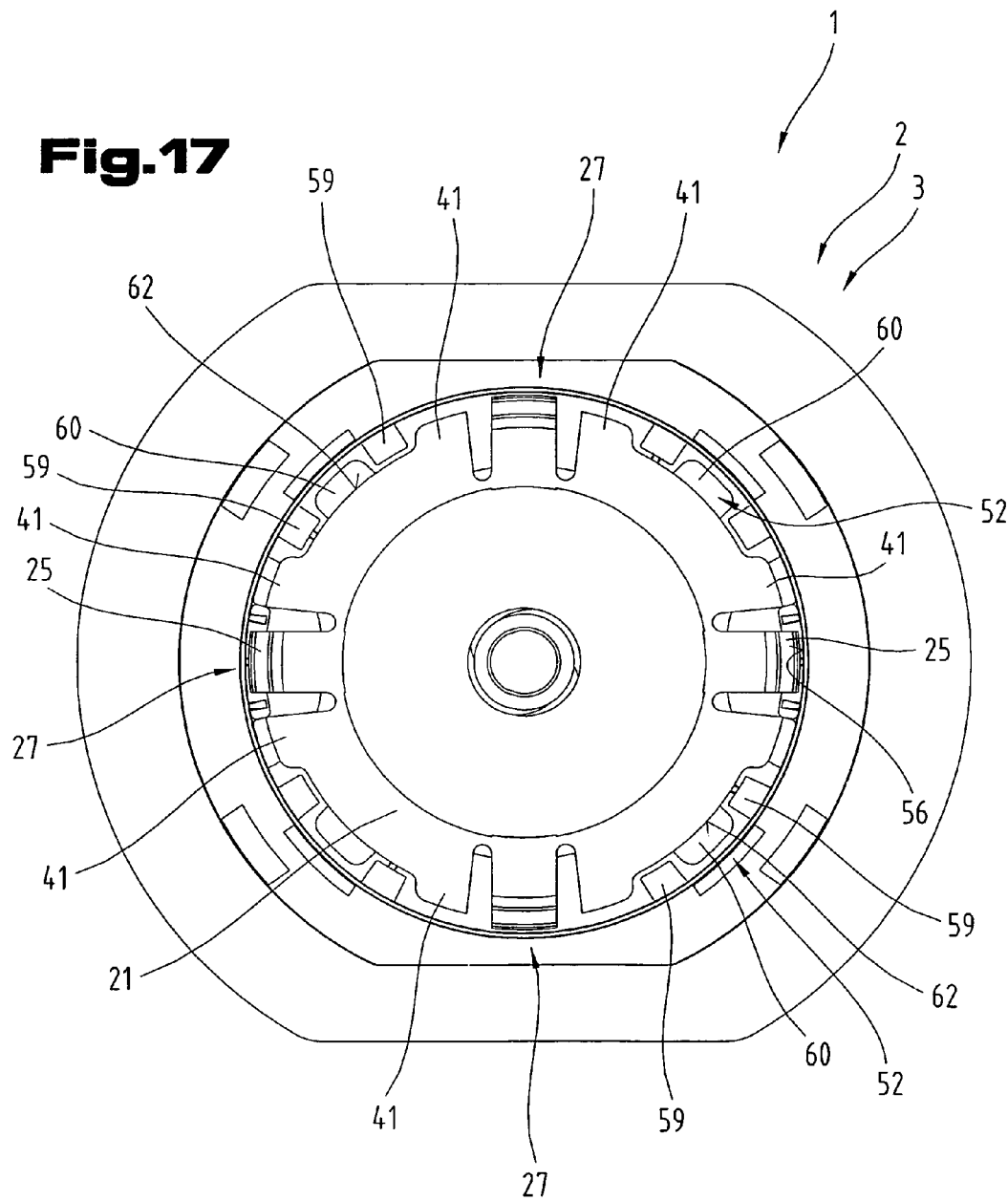

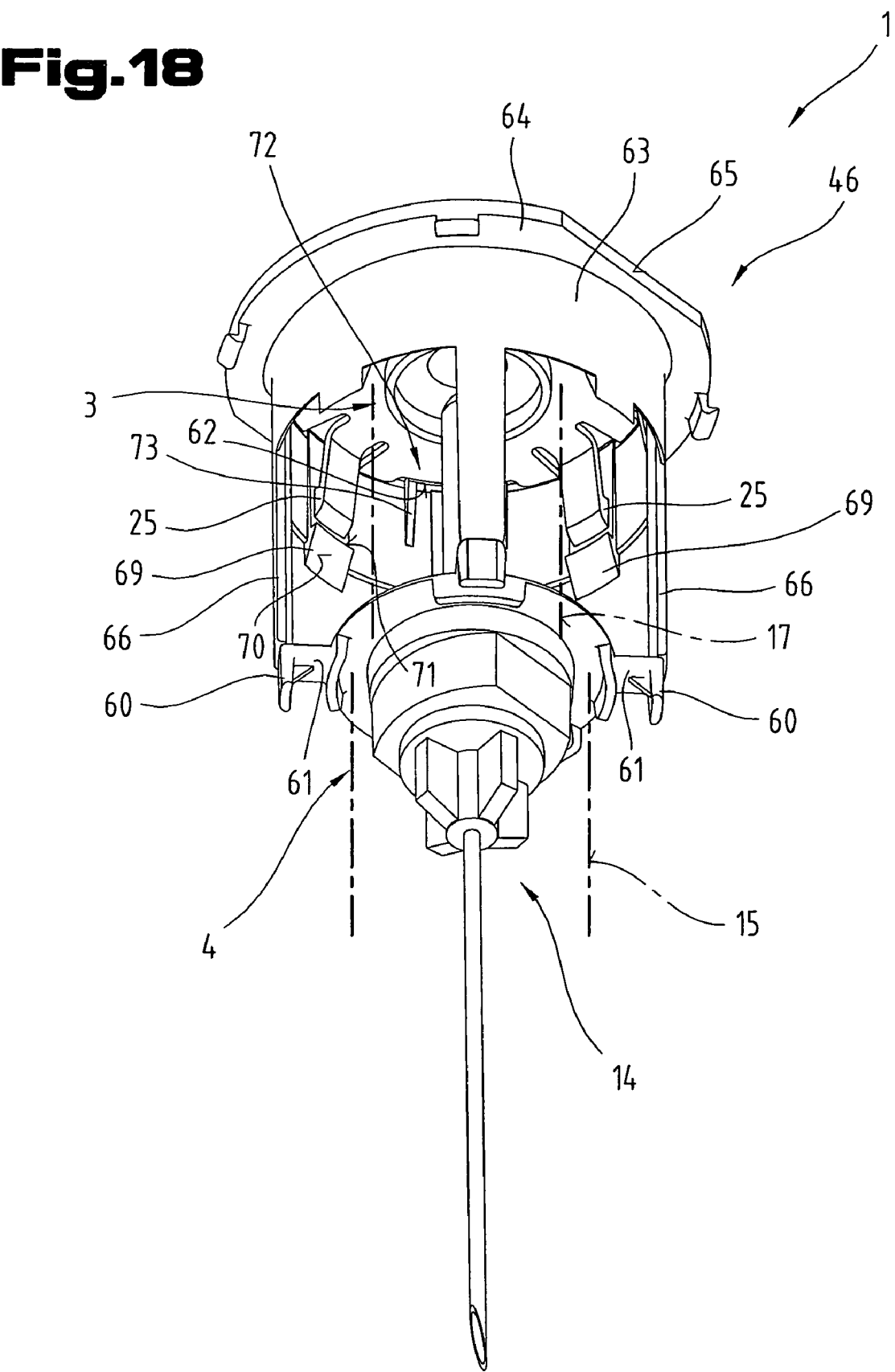

RECEIVING DEVICE COMPRISING AN ADJUSTABLE COVERING ELEMENT

CROSS REFERENCE TO RELATED APPLICATIONS

Applicant claims priority under 35 U.S.C. §119 of Austrian Applications Nos. A1492/2002 filed on Oct. 2, 2002 and Austrian A842/2003 May 30, 2003. Applicant also claims priority under 35 U.S.C. §365 of PCT/AT2003/000287 filed on Sep. 29, 2003. The international application under PCT article 21 (2) was not published in English.

The invention relates to a holding device with a holding container for a holding vessel, in particular a blood sample collecting tube, in which the holding container surrounds a holding chamber with a container wall, and in the direction of a longitudinal axis comprises a proximal and distal end spaced apart from one another, whereby the container wall is delimited by an inner surface facing the holding chamber and an outer surface facing away therefrom, with a needle holder for a needle arrangement that can be mounted therein, in particular a double-ended cannula needle, whereby the needle holder in the holding chamber of the holding container is designed to be displaceable relative to the latter as required from a position of use in the region of the proximal end to a disposal position in the direction of the distal end, with a first adjusting device for the needle holder for the required displacement from the position of use to the disposal position, with a cover element for the needle arrangement which can be mounted on the needle holder in the disposal position of the needle holder and with a releasable locking device.

A device for collecting blood is known from WO 01/93924A1, which comprises a holding container with a container wall, wherein the container wall surrounds a holding chamber and in the direction of a longitudinal axis has spaced apart ends. At the end of the holding container facing the patient for blood collection a needle holder with a needle arrangement mountable thereon, in particular a double-ended cannula, is provided. In addition, an adjusting device for the displacement from its position of use into the disposal position is assigned to the needle holder. A spring designed locking arm with a locking element arranged thereon is connected to the needle holder, which forms a locking device in cooperation with a locking recess in the container wall. In addition, a guide arrangement is provided between the needle holder and the container wall, by means of which during the relative displacement between the needle holder and the holding container, there can be a deflection from the straight movement of the needle holder inside the holding chamber and in this way an oblique position of the needle arrangement is achieved in the disposal position relative to the holding container. At the end facing away from the patient the holding container has an insertion element with a circular peripheral wall section, which in the disposal position covers an end of the needle arrangement facing the latter. In addition, in the disposal position in the region of the guide arrangement between the needle holder and the holding container in both movement directions at least one stop element can be arranged, in order to secure the needle holder and the needle arrangement located in the disposal position inside the holding container.

A further holding device with a holding container for a blood collecting tube is known from WO 92/20281 A1 in which the holding container surrounds a holding chamber with its container wall and in the direction of the longitudinal axis has spaced apart ends. Furthermore, the holding device comprises a needle holder displaceable from the position of use into the disposal position with a double-ended needle arrangement mounted therein. In the position of use the needle holder is located inside the holding chamber at the end of the holding device facing the patient, whereby one end of the needle projects out of the holding device and the other end projects over the needle holder in the direction of the holding chamber. In the container wall of the holding container in longitudinal extension thereof a slot-like recess is provided which is penetrated by a grip element connected to the needle holder, and the container wall projects to the side facing away from the holding container. The longitudinal, slot-like recess in the container wall also comprises several recesses arranged at right angles to its longitudinal extension, which are provided for interacting with the grip element in the various positions of the needle holder relative to the holding container and form a locking device. In the position of use of the needle holder one part of the grip element engages in one of these transverse recesses, whereby the needle holder together with the needle arrangement is held in position relative to the holding container. By means of the corresponding activation of the grip element the if necessary releasable locking device is released, and the needle holder can be pushed manually relative to the holding container into it disposal position. After a predeterminable displacement path of the needle holder both ends of the double-ended cannula are located inside the holding chamber, and there is a further engagement of the grip element in one of the aforementioned transverse recesses. Afterwards, an arc-shaped part of the grip element can be pivoted inwards by a further recess in the direction of the holding chamber, whereby a cover can be obtained between one end of the double-ended cannula and the open end region of the holding container.

A different holding device with a holding container for a blood sample collecting tube is known from WO 99/23947 A1, in which the holding container with its container wall surrounds a holding chamber and in the direction of a longitudinal axis has spaced apart ends. At the end facing the patient for collecting blood a double-ended needle arrangement is mounted in the direction of the longitudinal axis to be displaceable from its position of use into a disposal position. In the position of use one end of the double-ended needle arrangement projects over the holding container of the holding device into the side facing away from the holding chamber. Furthermore, the adjustable needle arrangement is allocated an adjusting device in the form of a spring element by means of which the needle arrangement is preloaded in the position of use by means of an if necessary releasable locking device. After the release of the locking device due to the spring adjusting device the needle arrangement is displaced relative to the holding container into the holding chamber of the holding container, whereby neither end of the double-ended cannula is freely accessible. The end of the double-ended cannula facing the holding chamber is also surrounded by a penetrable protective sleeve.

From U.S. Pat. No. 5,810,775 A a holding device for medical blood sample collecting tubes is known, in which by means of a pivot movement of the closing element relative to the holding container an adjustment element arranged in its holding chamber is adjusted by adjustment elements provided on the closing element in the direction of the longitudinal axis towards the proximal end, whereby the needle holder mounted in the region of the proximal end is released from its locked position in the adjustment element and after its release is returned by a preloaded spring element into the inner chamber of the holding device together with the needle arrangement. Because of the pivotal movement of the closing element in this embodiment there is, on the one hand, a longitudinal displacement of the adjusting element in the direction of the longitudinal axis, and, on the other hand, after releasing or unlocking the needle holder from the adjustment element the inner chamber of the holding device is sealed, whereby the operator is prevented from coming into contact with the needle arrangement. The disadvantage of this embodiment is that the connection between the needle holder and the adjusting element in the form of a locking fit is very expensive and has to be carried out precisely, in order, on the one hand, to obtain adequate fit for the collection process, and, on the other hand, to make sure the necessary releasing force for unlocking the connection is not too great. In addition, due to the spring preloading of the needle holder, if there is an unintentional release of the locked connection between the needle holder and the adjusting element, caused by the rapid return of the needle into the inner chamber, there is a high risk of injury to the user of this holding device.

A further holding device for blood collecting devices is known from U.S. Pat. No. 5,769,826 A or WO 98/41249 A1, in which a needle holder preloaded by a spring is held locked in the holding container by a slide in the position of use, and after the correctly performed collection procedure the lock between the slide and the needle holder can be released, whereby the latter is returned due to spring preloading with the needle arrangement into the inner chamber of the holding device. The distal end of said holding device is designed to be closable as necessary by a sealing element arranged pivotably on the holding container. The disadvantage here is that on activating the slide and the restoring movement associated therewith, due to the force of the spring preloading there is a return displacement of the needle holder into the inner chamber, whereby if the cap or sealing element is not closed operating personnel are at risk of needle sticks.

From the patent U.S. Pat. No. 5,407,436 A and WO 93/23098 A1 a holding container is known with a holding device for a needle holder and a double needle inserted therein, in which the needle holder equipped with the double needle can be retracted automatically into the inside of the holding container of the holding device after releasing a retaining device into the holding chamber. The needle holder is hereby fixed by securing elements at one end of the holding container, whereby between the front end and the needle holder a compressed and thus preloaded spring is arranged, which exerts force parallel to the longitudinal axis of the holding container onto the needle holder. By means of this force the needle holder is pressed against the holding catches of several securing elements. The securing elements are designed as finger-like projections of the holding container parallel to the middle longitudinal axis, and are arranged in such a way that they surround a disc-like shaped part of the needle holder over its circumference, and their holding catches aligned inwards in the direction of the middle longitudinal axis project so far over the edge of the disc-shaped part of the needle holder, that the latter is secured against the effect of the spring. In order to trigger the automatic retraction of the needle a tube-like plunger is used, which at the end to be inserted into the holding container of the holding device has an outwards pointing truncated-cone shaped tapering. If said plunger is pushed so far into the holding device that the truncated-cone shaped tapering is in contact with the holding catches, the securing elements with the holding catches are pressed apart to the side pointing away from the longitudinal axis, whereby the needle holder is released and displaced due to the spring force into the holding chamber. The disadvantage of this is that a separate component is needed for the release and single-handed operation is therefore not possible.

A further collecting device is known from U.S. Pat. No. 5,423,758 A and WO 95/16389 A1, in which the removal needle is held together with the needle holder in an adjustment sleeve and is surrounded by an additional protective sleeve, so that the removal needle is completely protected from the collecting process. A spring device is arranged between the needle holder and the outer protective sleeve. The needle holder is held by means of a clamping fit in the adjustment sleeve, whereby for appropriate use the adjustment sleeve is displaced relative to the outer protective sleeve, and then the spring device is preloaded. At the same time one end of the collecting needle moves out of the protective sleeve so that the collecting procedure can be performed. In this case the spacings or stops between a grip arranged on the adjustment sleeve and the protective sleeve interacting therewith are defined, so that for a correctly performed collecting procedure the spring device is only preloaded sufficiently that the secure fit of the needle holder in the adjustment sleeve is not released. In this position there is a mutual locking between the protective sleeve and the adjustment sleeve, in order to avoid repeated pulling apart between the latter. After the collection procedure the displaceable grip on the adjustment sleeve is moved into a further position spaced apart from the protective sleeve, whereby due to this spacing there can be a further relative displacement between the protective sleeve and the adjustment sleeve, and the secure fit of the needle holder is achieved by the preloaded spring device, and after releasing the secure fit the needle holder returns into the inner chamber of the adjustment sleeve. The disadvantage of this is that a large number of adjustment procedures need to be carried out between the individual components of the collecting device in order to ensure reliable functioning. At the same time it is possible to reach into the inside of the adjustment sleeve, which can result in unwanted needle stick injuries for the operating personnel.

A further safety collecting device is known from U.S. Pat. No. 2002/0099355 A1 in which the entire needle holder with the injection needle for the blood sample collecting tube arranged thereon and arranged at an angle in a separate longitudinal guide can be returned by an operator from the position of use to the disposal position. The disadvantage of this is that in the disposal position it is still possible to reach into the inner chamber of the holding device.

The objective of the invention is achieved in that the cover element is formed by an approximately disc-shaped main body arranged in a plane that is perpendicular to the longitudinal axis, whereby the cover element is arranged in the position of use of the needle holder adjacent to the latter on the side in the holding chamber averted from the proximal end, and in that the releasable locking device is arranged between the cover element and the holding container, with which the cover element is held in the position of use of the needle holder relative to the holding container, and in that a further adjusting device in the form of an elastically deformable spring element, in particular a compression spring, is arranged between the needle holder and the cover element, whereby on releasing the locking device the cover element is adjusted relative to the needle holder in the direction of the longitudinal axis by the additional adjusting device in the direction of the distal end of the holding container. The resulting surprising advantage of this is that in this way with the smallest longitudinal extension in the direction of the longitudinal axis, on the one hand, the insertion of the blood sample collecting tube for the correct collecting procedure and the injection procedure is made possible in one end of the cannula and, on the other hand, in the disposal position an operationally reliable covering of this cannula end is made possible. Furthermore, by means of the immediately adjacent arrangement of the needle holder and the cover element inside the holding container, the entire holding device is ready for appropriate use without any need for preparative steps, and the locking device can be released by the respective operator single-handedly. This can be achieved very easily by the arrangement of the locking device on the holding container by the preloaded and locked cover element in cooperation with the also preloaded needle holder. In this way, on the one hand, the needle holder is held in position in the direction of the longitudinal axis of the holding container in its position of use and, on the other hand, after releasing the locking device the cover element by means of this additional adjusting device is arranged with simultaneous displacement of the needle holder spaced apart from the latter in the disposal position inside the holding container, and thus the automatic covering of one needle end of the needle arrangement is ensured. In this way, on the one hand, a safe operation is ensured and once the collecting procedure has been completed a secure closure of the inner chamber by the cover element for the cannula end facing the inner chamber or the distal end is achieved. In this way unintentional access to the inner chamber and the risk of unwanted needle stick injury is prevented, whereby the risk of infection to the operator is much reduced, if not eliminated. At the same time however an inexpensive holding device is created which requires only a small number of components and at the same offers a high degree of operational safety.

A further embodiment according to claim 2 is also advantageous as thereby the needle holder can also be returned safely into its disposal position even after a longer storage period, and thus a high degree of operational safety is ensured. It is also advantageous in this case that by a simple operation, in particular a single-handed operation. there is not need for additional sequences to be carried out merely due to the symmetrical release of the locking device, and thus the end of the needle arrangement designed for removal or collection, for example from the arteries or veins of a patient, can be withdrawn by the first adjusting device without further changing of position of the holding container relative to the patient. At the same time, the other end of the double-ended cannula is also covered in the region of the distal end, whereby access and thus associated needle stick injury is reliably prevented from both ends of the cannula. In this way a simple one-handed operation is possible, in which the two ends of the needle arrangement are arranged inside the holding container, and in the region of the distal end unintentional needle stick injury can be avoided.

A design according to claim 3 is also advantageous, as thereby, on the one hand, the needle holder is positioned in the direction of the longitudinal axis of the holding container in its position of use, and, on the other hand, after releasing the locking device the cover element is arranged by means of the further adjusting device with a simultaneous adjustment of the needle holder spaced apart from the latter in the disposal position inside the holding container, and thus the automatic covering of one needle end of the needle arrangement is ensured.

By means of the design according to claim 4 it is possible to arrange the needle holder between the two adjusting devices, whereby the insertion of the needle holder from the larger end to the smaller end is made possible.

According to a different embodiment according to claim 5 a simple structural unit is created, inside which the needle holder can be clamped between the windings, and thus, on the one hand, there can be a precise longitudinal positioning in the direction of the longitudinal axis of the holding container and, on the other hand, a compact structural unit can be obtained. Furthermore, by means of the conically expanding additional adjusting devices the assembly of the needle holder with the adjusting device can be much simplified.

In the design according to claim 5 it is an advantage, on the one hand, that there can be an unhindered longitudinal displacement of the cover element in the direction of the longitudinal axis, inside the holding chamber, and, on the other hand, at the same time the holding chamber is covered by the cover element over a large part of the cross-sectional surface.

By means of the development according to claim 8, with the least space in the position of use the end of the cannula facing the blood sample collecting tube can penetrate the cover element, and in the disposal position despite this the cover element can securely cover this end.

By means of the design according to claim 9 residue on the cannula needle or the protective sheath surrounding the latter can be suctioned off or removed during the relative adjustment movement between the cover element and the needle holder, and thus infection caused by spraying out of individual particles, especially body fluids such as blood or the like, can be prevented.

A design according to claim 10 is also advantageous as thereby, on the one hand, the cover element can be mounted securely and in association with this the needle holder can be secured inside the holding container, and, on the other hand, the user can perform an even release by means of the diametrically opposite locking elements. In this way the tilting of the components to be adjusted inside the holding container is also prevented.

According to the designs described in claims 11 to 13, a simple interaction of the locking elements on the cover element with the locking recesses arranged in the container wall can be achieved, whereby here a simple operation i.e. simple pressure in the direction of the longitudinal axis, i.e. the centre of the holding container, is performed for releasing the locking device. Due to the multiple arrangement of the locking elements on the cover element on releasing the locking device by means of the additional locking elements the cover element can be supported or centred relative to the holding container, whereby a secure release with a simultaneously associated guiding performed immediately afterwards is achieved during the entire adjustment up to the disposal position.

The design according to claim 14 is also advantageous, as thereby a simple operation of the locking device is made possible from the outside of the holding container.

As described in claim 15, on the one hand, an unintentional release due to the possible projection of the locking elements on the outer surface of the container wall is prevented, and, on the other hand, the required displacement path for triggering the locking device is set to a predeterminable path, in order to prevent misuse or unintentional triggering.

A design according to claim 16 is advantageous, as thereby there is continuously a secure locking of the locking device in the position of use and thus a high degree of operational safety is achieved for the entire holding device.

According to the designs described in claims 17 and 18, the main body is spaced apart from the inner surface of the holding container, whereby the guiding arrangement between the cover element and the holding container is reduced to a small area viewed in radial direction relative to the entire circumference and thus a smooth and tilt-free guiding arrangement is provided.

A further development according to claim 19 is also advantageous, as in this way, on the one hand, for the assembly procedure and, on the other hand, over the entire displacement of the cover element between its two end positions, the adjusting device is constantly held in a predeterminable position on the main body and thereby a smooth sequence of movement is ensured.

According to advantageous developments according to claims 20 to 23, during the relative adjustment of the cover element in the direction of the longitudinal axis relative to the holding container, a tilt-free longitudinal movement is ensured, without the cover element being able to rotate about the longitudinal axis.

In the design according to claim 24 it is advantageous, that over the entire displacement path of the cover element the distance between the groove base of the guiding groove and the longitudinal axis is constant. In this way a secure longitudinal adjustment of the cover element is achieved between its two end positions.

The design according to claim 25 ensures with a perfect guiding in the direction of the longitudinal axis an aligned arrangement and releasing of the locking device.

A further embodiment according to claim 26 is also advantageous, as thereby also the cover element is guided continually over its entire longitudinal movement in the direction of the longitudinal axis between its two end positions, and thus a high degree of operational safety of the entire holding device can be achieved.

A development according to claim 27 is also advantageous, as in this way a parallel alignment of the guide tracks relative to the longitudinal axis is achieved, and thus over the entire displacement path the distance between the longitudinal axis and the guide tracks remains the same.

By means of the design according to claim 28, it is possible to achieve perfect guiding between the position of use and the disposal position of the parts to be displaced inside the holding container, whereby a high degree of operational safety and thereby sufficient protection for the operating personnel is ensured.

Further advantageous design of the guiding arrangement are described in claims 29 to 31.

The advantage in this case is that by means of the bearing force applied by the locking elements on the guide track, the cover element is always aligned centrally to the longitudinal axis, and due to the predeterminable bearing force constant frictional ratios, provided there is a constant surface quality, can be achieved for the entire displacement.

Further advantageous designs of the additional guiding arrangement are characterised in claims 32 to 34, whereby for the needle holder a predetermined, straight guiding arrangement has also been provided, by means of which a secure adjustment of the latter from the position of use to the disposal position is made possible. By means of the multiple arrangement of the guiding elements a tilt-free and mainly rotationally secure longitudinal movement is performed.

By means of the design according to claim 36, in addition to the guiding elements in the region of the inner surface of the holding container an additional further guiding possibility is created, whereby the needle holder can be adjusted more precisely in the direction of the longitudinal axis.

By means of the further developments of the additional guide arrangement, according to claims 37 to 40, on the one hand, a precise and mainly rotationally secure longitudinal guiding of the needle holder is achieved in the region of the inner surface of the holding container, and, on the other hand a longitudinal movement into the disposal position is ensured, so that the risk of injury to the operating personnel is much reduced.

The design according to claim 41 is advantageous, as thereby longitudinal displacement can occur in the region between the cover element and the inner surface of the holding container, whereby unintentional access to the inner chamber of the holding container closed off by the cover element is reliably prevented.

According to claim 42 the simple insertion of the structural unit formed by the needle holder and the cover element into the holding container is made possible, whereby support is provided in the region of the other end for the structural unit spring-mounted there.

In the design according to claim 43 in the region of the end wall a longitudinal guide for the needle holder is created, in order to absorb lateral loads during correct usage, and then after the correct usage to permit a simple sliding movement between said components.

According to claim 44 for the adjusting device a holding chamber for the adjusting device separate from the needle holder is made possible, in order over the smallest area to store a sufficient restoring force applied by the adjusting device, and in addition to prevent clampinging between the components during appropriate use.

By means of the design according to claim 45 a double-ended collection needle can be inserted in the sleeve-shaped carrier body, whereby in the region of the outer surface there can be additional support on the holding container.

In the design according to claim 46 it is advantageous that here the adjusting devices can be supported to secure the position of the entire needle holder during its correct usage in: the position of use.

Advantageous designs and arrangements of the adjusting devices on the support element are described in claims 47 to 49, as thereby with defined positioning of the needle holder relative to the holding container, also during assembly, a simple and mainly easily assembled structural unit is created.

Further advantageous designs of the needle holder are described in claims 50 to 52, whereby all-round continuous support for the first adjusting device with simultaneous centering of the latter relative to the needle holder can be achieved. By means of the tubular depression for the additional adjusting device a predeterminable support position is created, whereby the needle holder is positioned between the two adjusting devices, and thus a high degree of operational safety can be achieved. Furthermore, the centring element can also be used for the oriented alignment of the needle holder for insertion into the holding container, in order to be able thus to secure the alignment of the needle arrangement to be used into the thread arrangement relative to the locking device.

As described in claims 53 to 54 a predefined positioning of the cannula tip, in particular the tapered section for the insertion of the needle, can be created relative to the locking device, in order to permit simple one-handed use without the risk of a stick injury caused by otherwise necessary adjustment procedures.

By means of the design according to claim 55 simple handling is achieved for the use of the collecting needle in the needle holder, as here the entire collecting container can be held simply, and the collecting needle can be simply screwed into the needle holder without requiring further fixing.

Further advantageous designs of the cover element and the holding container are characterised in claims 56 to 59, whereby a repeat return of the cover element into the holding chamber of the holding container is prevented, and thus an undesired stick injury can be prevented along with the associated risk of possible infection.

In the design according to claim 60 an undesired removal of the cover element from of the holding chamber of the holding container is prevented, whereby in cooperation with the restoring elements, clear fixing of position in the direction of the longitudinal axis is created. Furthermore, in this way the spring force of the adjusting devices can be increased, as thus an undesired removal is reliably prevented.

A design as described in claim 61 is also possible, as thereby an additional anti-rotational means for the cover element about the longitudinal axis relative to the holding container is provided.

By means of the developments according to claims 62 and 63 in the region of the distal end, on the one hand, the assembly is made simple with a not yet inserted securing element, and on the other hand, after the insertion of the securing element into the holding container the entire holding device has a high degree of operational safety.

A design according to claim 64 is also advantageous, as thereby a precise insertion of the securing element into the distal end of the holding container is possible, and at the same time in cooperation with the flange-shaped step a definite positioning inside the holding container can be achieved.

Developments according to claims 65 to 68 are also advantageous, as in this case, on the one hand, the insertion of the securing elements is made easy by the projecting positioning elements, and on the other hand, a stop for the displacement path of the needle holder, and thereby a secure positioning of the latter inside the holding container in is achieved in the disposal position. In this way the needle holder can be pressurised with a greater spring force by the adjusting device, by means of which the latter is then pressed securely against the positioning elements.

Other designs are also possible, in which the cover element in the disposal position of the holding device in both directions is held in the direction of the longitudinal axis on the securing element. In this way the cover element can be pressurised by the additional adjusting device with a greater spring force, in order to achieve a secure adjustment of the latter to the disposal position. This is mainly significant for the locking elements arranged on the holding arm, as the latter have to be adjusted to obtain the disposal position by means of the retaining elements, in order to reach the disposal position.

Finally, an embodiment is advantageous, in which even in the disposal position, pivoting and rotation about the longitudinal axis are prevented, and thus subsequent manipulation is prevented. In this way, on the one hand, injury to the operating personnel can be prevented, and on the other hand, the reuse of the entire holding device with the already unlocked locking device can also be prevented.

The invention is explained in more detail in the following with reference to the embodiments illustrated in the drawings.

FIG. 3 shows the holding container for the holding device according to FIGS. 1 and 2, in diagrammatically simplified view;

FIG. 4 shows the holding container according to FIG. 3 in a different, diagrammatically simplified view;

FIG. 5 shows the needle holder for the holding device according to FIGS. 1 and 2 with a needle arrangement inserted therein in a diagrammatically simplified view;

FIG. 6 shows the cover element for the holding device according to FIGS. 1 and 2 in diagrammatically simplified view;

FIG. 11 shows the cover element according to FIGS. 7 and 8 in simplified perspective view;

FIG. 12 shows the cover element according to FIG. 11 in a different simplified perspective view;

FIG. 17 shows the holding device according to FIGS. 7 and 8 in a view of the distal end but with a removed securing element;

FIG. 18 shows the holding device according to FIGS. 7 and 8 in a simplified perspective view in its disposal position, but with removed holding container and a modification of the anti-rotational means in the region of the needle holder compared to the view in FIGS. 13 and 14.

Figure 1:
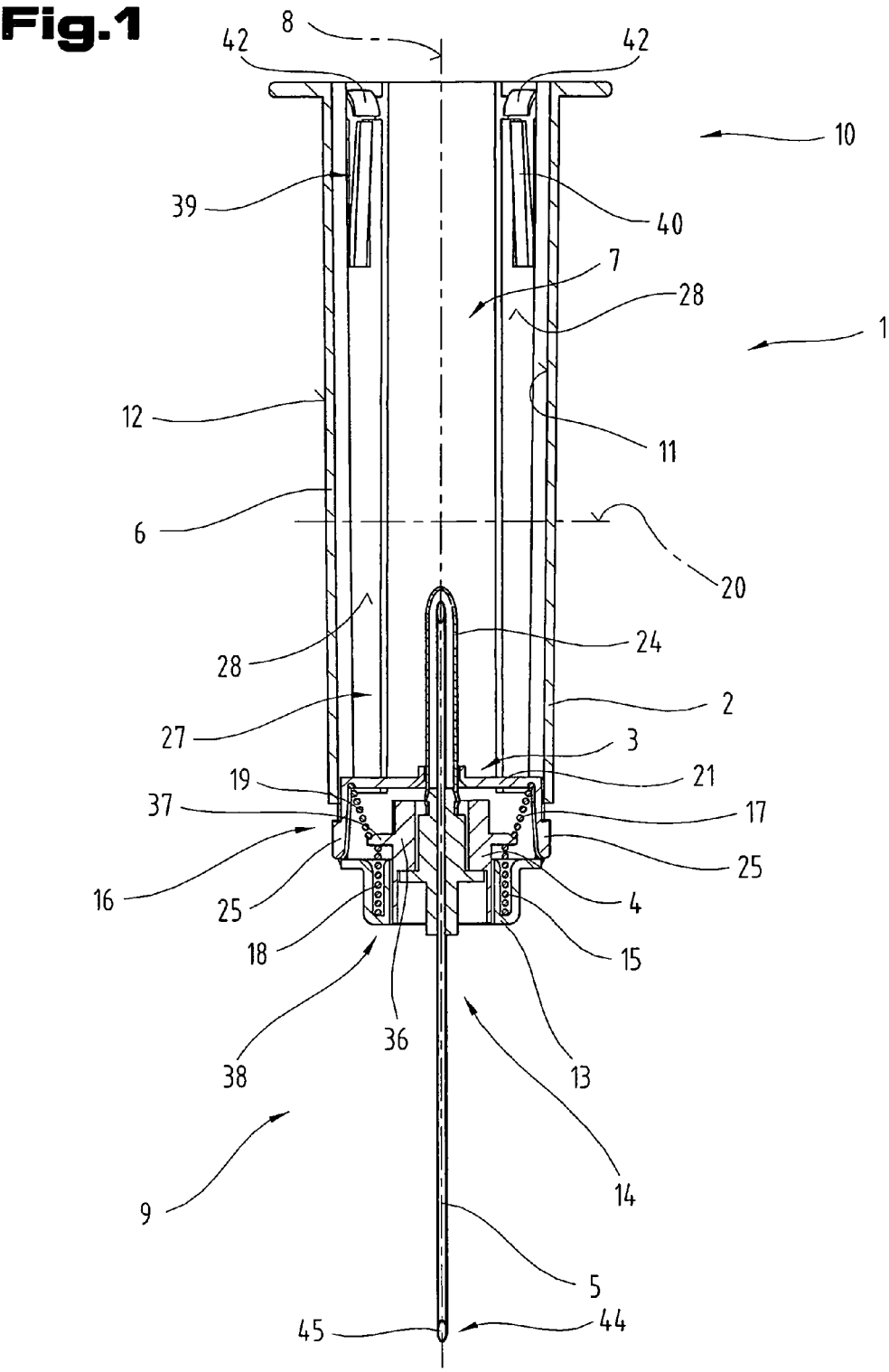
FIG. 1 shows a side view of the holding device according to the invention in cross section, and in a simplified schematic view, in its position of use.

First of all, it should be mentioned that in the various embodiments described the same parts are allocated the same reference numbers and the same component names, whereby the disclosures contained in the entire description can be applied to the same parts with the same reference numbers or same component names. In addition, the descriptions of positions such as e.g. top, bottom, side etc. refer to the drawing currently being described, and when the position changes should be understood to apply to the new position. Furthermore, individual features or combinations of features from the various embodiments shown and described can represent independent, inventive solutions of the invention.

In FIGS. 1 to 6 a holding device 1 for a holding vessel, not shown here in detail, such as a generally known blood sample tube, is illustrated in a simplified manner, and the latter comprises an outer holding container 2 and cover element 3 inserted therein and a needle holder 4 with a mostly double-ended cannula needle 5.

The holding container 2 has a longitudinal shape and defines a holding chamber 7 with its container wall 6. In the direction of the longitudinal axis 8 the holding device 1 or the holding container 2 comprises a proximal end 9 and a distal end 10 spaced apart from one another. The container wall 6 is delimited by an inner surface 11 facing the holding chamber 7 and an outer surface 12 facing away from the latter. In the embodiment shown here one of the two ends—in the present embodiment the distal end 10 is designed to be open and the other end—here the proximal end 9—is designed to be at least partly closed. The proximal end 9, which is partly closed here, is partially closed by an end wall 13.

In general, it should be pointed out that the two ends 9, 10 have been named from the perspective of the patient. Thus the proximal end 9 faces the patient and the distal end 10 is furthest away from the latter.

In the position of use of the needle holder 4 and a needle arrangement 14 mountable therein shown in FIG. 1, which in the present embodiment is in the form of a double-ended cannula 5, one end, which is designed for inserting into a living being or a collecting vessel, projects over the end wall 13 in the direction opposite the holding chamber 7. The other end of the cannula 5 projects over a partial section into the holding chamber 7 of the holding container 2, whereby in a known manner a holding vessel not shown in more detail here, in particular a blood sample collecting tube is inserted into the holding chamber 7 and the sealing device of the blood sample collecting tube is pierced by this end of the cannula 5, and thus a connection via the cannula 5 can be made with the inner chamber of the blood sample collecting tube. Furthermore, the needle holder 4 in the holding chamber 7 of the holding container 2 is designed to be displaceable relative to the latter, as required from the position of use shown in FIG. 1 in the region of the proximal end 9 in the direction of the distal end 10 into a disposal position according to FIG. 2.

In addition, a first adjusting device 15 for the displacement from the position of use into the disposal position is allocated to the needle holder 4. The cover element 3 is arranged in FIG. 1—the position of use of the needle arrangement 14—immediately adjacent to the needle holder 4 on the side facing away from the proximal end 9 in the holding chamber 7. Between the cover element 3 and the holding container 2 of the holding device 1 it is also shown in FIG. 1, that here a releasable locking device 16 is arranged, by which the cover element 3 is held in the position of use relative to the holding container. Furthermore, between the needle holder 4 and the cover element 3 a further adjusting device 17 is arranged, whereby on releasing the locking device 16 the cover element 3 is adjusted by the additional adjusting device 17 in the direction of the distal end 10 of the holding container 2.

Thus, on the one hand, on the side facing the end wall 13 the first adjusting device 15 and, on the other hand, on the side facing the cover element 3 the additional adjusting device 17 is allocated to the needle carrier 4 and by means of these two adjusting devices 15, 17 is mounted in the position use in the direction of the longitudinal axis 8. The additional adjusting device 17, as already described above, is arranged between the needle holder 4 and the cover element 3, whereby by means of the locking device 16 the cover element 3 is secured in position relative to the holding container 2, if necessary detachably.

Advantageously, the first adjusting device 15 and/or the additional adjusting device 17 are both formed by an elastically deformable spring element 18, 19, in particular a compression spring. Said compression springs can be made from various different materials and have various different deformation and spring properties, whereby preferably spiral springs are used. It is also advantageous if the additional adjusting device 17 is designed to expand conically from the needle holder 4 to the cover element 3, as is shown in a simplified view in FIG. 2. Regardless of this it is also possible to design the first and the additional adjusting device 15, 17 as a one-piece component, as in this way the assembly cost and the number of individual parts can be reduced.

Due to the arrangement of the two adjusting devices 15, 17 both the needle holder 4 and the cover element 3 are adjusted simultaneously from the position of use into the disposal position after releasing the locking device 16.

The cover element 3 is in this embodiment in the form of a roughly disc-shaped main body 21 lying in a plane 20 perpendicular to the longitudinal axis 8.

As already described, the end of the cannula 5 facing the blood sample collecting tube and thereby the holding chamber 7 in the region of the longitudinal axis 8 passes through an opening 22. Furthermore, it is shown in simplified manner in FIG. 2, that in the region of the opening 22 a component 23 for suctioning or absorbing a fluid can be arranged, which can be penetrated by the cannula 5 or the protective sleeve 24 arranged over the latter and shown in simplified form. Said component 23 serves to absorb or suction up any possible residue found in the region of the cannula 5 or on the protective sleeve 24, in particular drops of blood, during the relative displacement between the needle holder 4 and the cover element 3, determined by the displacement device 17, in order to avoid spraying out and possible infection of the operator.

The locking device 16 comprises at least one, preferably two, diametrically opposite locking elements 25 and locking recesses 26 cooperating with the latter. In this embodiment the locking element or elements 25 is or are arranged on the disc-shaped main body 21 of the cover element 3, whereby the locking recesses 26 are arranged in the container wall 6 of the holding container 2, and pass through the latter to release the locking elements 25 from outside the holding container 2. In order to prevent the unintentional release of the locking elements 25 from the locking recesses 26, it is advantageous if the locking element or elements 25 project in radial direction from the inner surface 11 to the outer surface 12 of the container wall only partially into the locking recesses 26. In this way the release path is reduced in radial direction to the longitudinal axis 8 and at the same time the risk of incorrect use or unintentional release is reduced. The locking element or elements 25 are resiliently connected, for example by a web, with the disc-shaped main body 21 of the cover element 3. In this case the locking elements 25 project by means of the resilient web in the direction of the needle holder 4 from a disc-shaped main body 21.

Furthermore, between the cover element 3 and the inner surface 11 of the container wall 6 at least one guiding arrangement 27 can be provided, by means of which the cover element 3 can be displaced in an exclusively longitudinal movement in the direction of the longitudinal axis 8 from the position of use into the disposal position in the region of the distal without rotation occurring about the longitudinal axis 8. Said guiding arrangement 27 is formed by at least one guiding groove 28 indented in the container wall 6 and running in the direction of the longitudinal axis 8, and forms at least one guide extension 29 on the cover element 3 engaging in the guiding groove 28. In order to achieve a tilt-free longitudinal adjustment in the direction of the longitudinal axis 8 it is advantageous if several guiding grooves 28 are arranged, distributed evenly around the circumference of the holding container 2, with which several guide extensions 29 of the cover element 3 engage. With a diametrically opposite arrangement of the locking devices 16 the latter are arranged viewed in the direction of the longitudinal axis 8 around the circumference of the holding container 2 symmetrically between the guiding grooves 28, as thus, on the one hand, a perfect release and, on the other hand, an unhindered longitudinal adjustment of the cover element 3 can be achieved in the direction of the longitudinal axis 8 inside the holding container 2. It is also advantageous if a groove base of the guiding groove 28 over its longitudinal extension relative tot the longitudinal axis 8 runs parallel to the latter.

The container wall 6 has a circular cross section in the plane 20 perpendicular to the longitudinal axis 8, whereby an outer diameter 30 of the disc-shaped main body 21 corresponds approximately to an inner diameter 31 of the holding chamber 7 in the same plane or is only slightly smaller. In this way it is ensured that, on the one hand, there can be an unrestricted longitudinal displacement of the cover element 3 in the direction of the longitudinal axis 8 inside the holding chamber 7, and on the other hand, at the same time the holding chamber 7 is covered by the cover element 3 over a large part of the cross section surface.

The holding container 2 is open in the region of the distal end and in the region of the proximal end 9 is partially closed by the end wall 13. In this way, in the region of the proximal end 9 it is possible to support the compression forces exerted by the adjusting device 15 on the end wall 13. Furthermore, an opening 32 is arranged in the end wall 13 in the region of the longitudinal axis 8, which in its cross sectional dimension 33 corresponds approximately to an outer cross sectional diameter 34 of the needle holder 4. In this way, as can best be seen from FIG. 1, a partial section of the needle holder 4 can project into the opening 32, whereby the insertion of the needle arrangement 14, in particular the cannula 5, into the needle holder 4 can be made easier.

Furthermore, in the end wall 13 there is a holding chamber 35 for the first adjusting device 15 or the one-piece component formed by the adjusting devices 15, 17. In this way in the smallest space both the needle holder in its bearing, guided in the direction of the longitudinal axis 8, and the adjusting device 15 or the component formed by the latter, can be mounted and secured separately therefrom.

The needle holder 4 is in the form of a sleeve-shaped supporting body 36, whereby in the plane 20 perpendicular to the longitudinal axis 8 at least one support element 37 is arranged thereon which projects radially outwards over the latter. Said support element 37 is preferably designed to be continuous around the circumference and is used, so that the adjusting devices 15, 17 are supported on the respectively facing end regions. It is also possible however to arrange several support elements 37 around the circumference on the supporting body 36. For better securing of the needle holder 4 relative to the adjusting devices 15, 17 it is advantageous if at least one of the end regions is secured to the support element 37. In this way the cost of final assembly can be reduced. With a one-piece design of the adjusting device 15, 17 the support element 37 is arranged in a transition region of the latter and mounted on the one-piece component. If, as already described, the additional adjusting device 17 or the part of the one piece component forming the latter is designed to be conical in the direction of the distal end 10, the use of the needle holder 4 with the support element arranged thereon is possible up to the transition area, whereby then the support element 37 can be inserted and secured accordingly between the windings of the adjusting device.

Furthermore, it can also be seen from FIG. 3, that in the region of the opening 32 in the end wall 13 between the latter and the portion of the needle holder 4 projecting into the opening 32 (cf. FIG. 1) an anti-rotational means 38 is arranged, which is in engagement in the position of use of the needle holder 4, and prevents relative pivoting or rotation between the holding container 2 and the needle holder 4 about the longitudinal axis 8. This anti-rotational means 38 is in the present embodiment in the form of a flattened section on the supporting body 36, and in the region of the opening 32 has corresponding, mutually designed stop surfaces. In this way a longitudinal movement of the needle holder 4 in the direction of the longitudinal axis 8 is possible but rotation is prevented about the longitudinal axis 8 in the position of use.

Figure 2:
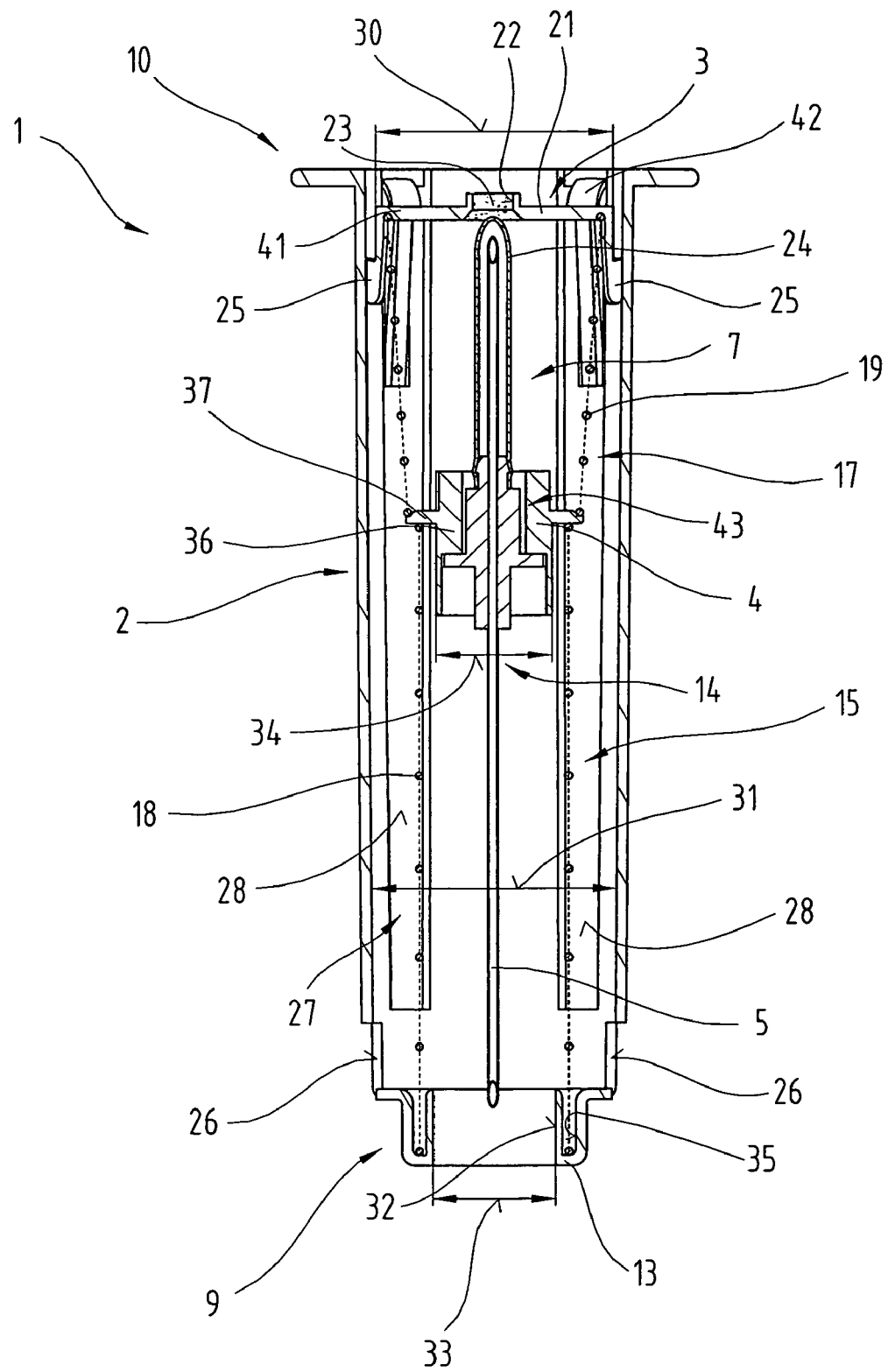
FIG. 2 shows the holding device according to FIG. 1 in the disposal position of the needle holder and simplified schematic view.

Furthermore, as can be seen from an overview of FIGS. 1, 2 and 4, if the needle holder 4 is in the disposal position, the cover 3 element is moved into the region of the distal end—according to drawing FIG. 2—by the interaction of the adjusting devices 15, 17 and is secured there relative to the holding container 2 in its longitudinal movement in the direction of the longitudinal axis 8 by means of a locking device 39. In this embodiment the locking device 39 is formed by at least one retaining element 40 arranged on the holding container 2 and facing the distal end 10, and at least one locking elements 41 cooperating therewith on the cover element 3. In this way the retaining element or elements 40 can be formed respectively by a spring section of the container wall 6, which are designed to project over at least a portion of their longitudinal extension in the direction of the longitudinal axis 8 over the inner surface 11 in the direction of the longitudinal axis 8. Due to the resilient design of this retaining element 40 movement of the cover element 3 from the proximal end 9 towards the distal end 10 is made possible, whereby the retaining elements 40 are displaced radially outwards against their spring effect to the side facing away from the longitudinal axis 8 and thus the passage of the cover element 3 is made possible up to the renewed expansion of the retaining elements 40.

If the retaining elements 40 are returned or expanded to their original position, movement of the cover element 3 in the direction of the proximal end 9 is prevented. In this way unintentional access to the holding chamber 7 of the holding container 2 and the needle arrangement 14 located therein is reliably prevented. In order to avoid the exit of the cover element 3 during the displacement movement into the disposal position out of the holding chamber 7 of the holding container 2, the locking device 39 also comprises at least one stop element 42 for the cover element 3 arranged on the holding container 2 and facing the distal end 10. In this way the cover element 3, viewed in the direction of the longitudinal axis 8, is secured on both sides from moving, and is thus secured in the disposal position.

The retaining element or elements 40 is or are arranged in the region of the guiding arrangement 27, in particular in the guiding groove 28 in the end region facing the distal end 10. At the same time however the stop element or elements 42 are arranged in the region of the guiding arrangement 27, in particular in the guiding groove 28.

As is generally known, in the sleeve-shaped supporting body 36 of the needle holder 4 a thread arrangement 43 for the needle arrangement 14 is arranged, whereby the thread arrangement 43 is aligned, so that with an opposite arrangement and horizontal alignment of the releasable locking device 16 for the cover element 3 a tapering 45 on a cannula tip 44 is arranged on an upper side of the cannula 5, as can best be seen from FIG. 1. In this way for the drawing procedure or appropriate use the entire holding device 1 can be held, for example in a right-handed operation, by the thumb and index finger and already in the region of the locking device 16, whereby at the same time the cannula 5 is arranged in the correct position for the collecting procedure, namely with the tapering on the visible side of the cannula 5 facing the user. In this way a continually aligned position is ensured after the insertion of the needle arrangement 14 into the needle holder 4 relative to the entire holding device 1. Any rotation or displacement or additional manipulation of the cannula and the associated risk of stick injury is thus very unlikely if not eliminated.

In FIGS. 7 to 17 a further possibility of a design of the holding device 1 is shown in simplified form for a holding vessel, not shown in detail here, such as for example a generally known blood sample tube. At the same time the same reference numbers and names are used for the same parts. In order to avoid unnecessary repetition reference is made to the detailed description in the preceding FIGS. 1 to 6. FIG. 18 basically shows the components shown in FIGS. 7 to 17, but with a modification of the anti-rotational means 38 between the needle holder 4 and the holding container 2. The holding device 1 comprises in this embodiment the holding container 2, the cover element 3, the needle holder 4 with the needle arrangement 14 inserted or insertable therein, mostly the double-ended cannula 5. In addition, the holding device 1 comprises in the region of the distal end 10 of the holding container 2 at least one securing element 46 inserted therein, which is shown in simplified and schematic form in perspective view in FIGS. 15 and 16.

Figure 7:
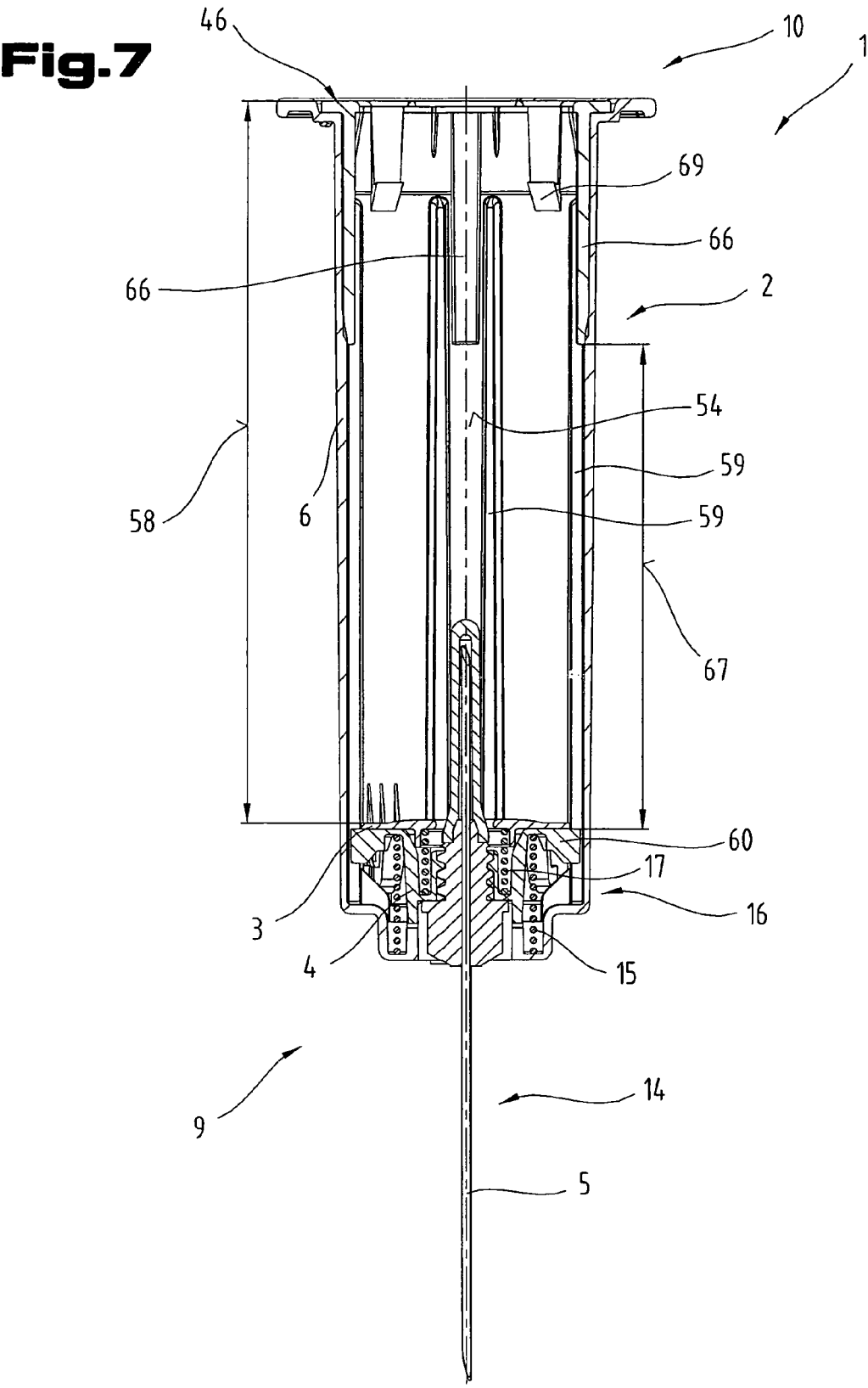
FIG. 7 shows an additional holding device in the position of use, in cross section in side view and simplified schematic view.

FIG. 7 shows, as already illustrated in FIG. 1, the position of use in which the needle holder 4 with the cannula inserted or insertable therein and the cover element 3 in the region of the proximal end 9 of the holding container 2, and the two adjusting devices 15, 17 are in a preloaded position, from which the latter after unlocking the locking device 16 move or adjust the needle holder 4 and the cover element 3 into the disposal position by means of the spring force acting on said parts. Said adjustment procedure has already been described in detail in the preceding FIGS. 1 to 6 and is not discussed further at this point.

The securing element 46 is inserted into the holding chamber 7 of the holding container 2 and can be locked or is locked onto the latter. In this way it is possible to insert the needle holder 4, the cover element 3, and if necessary the cannula 5, and the adjusting devices 15, 17 or an individual component formed from these two components into the holding chamber 7 of the holding container 2, and to position the locking device 16 in the region of the proximal end 9 in its locked position and only then use the securing element 46 afterwards. In this way the assembly is simplified, as over the entire insertion of the previously described individual parts in the region of the proximal end 9 the holding container 2 in the region of its distal end 10 has no retaining or stop elements, and thus the insertion procedure can be performed easily and mostly unhindered.

Figure 8:
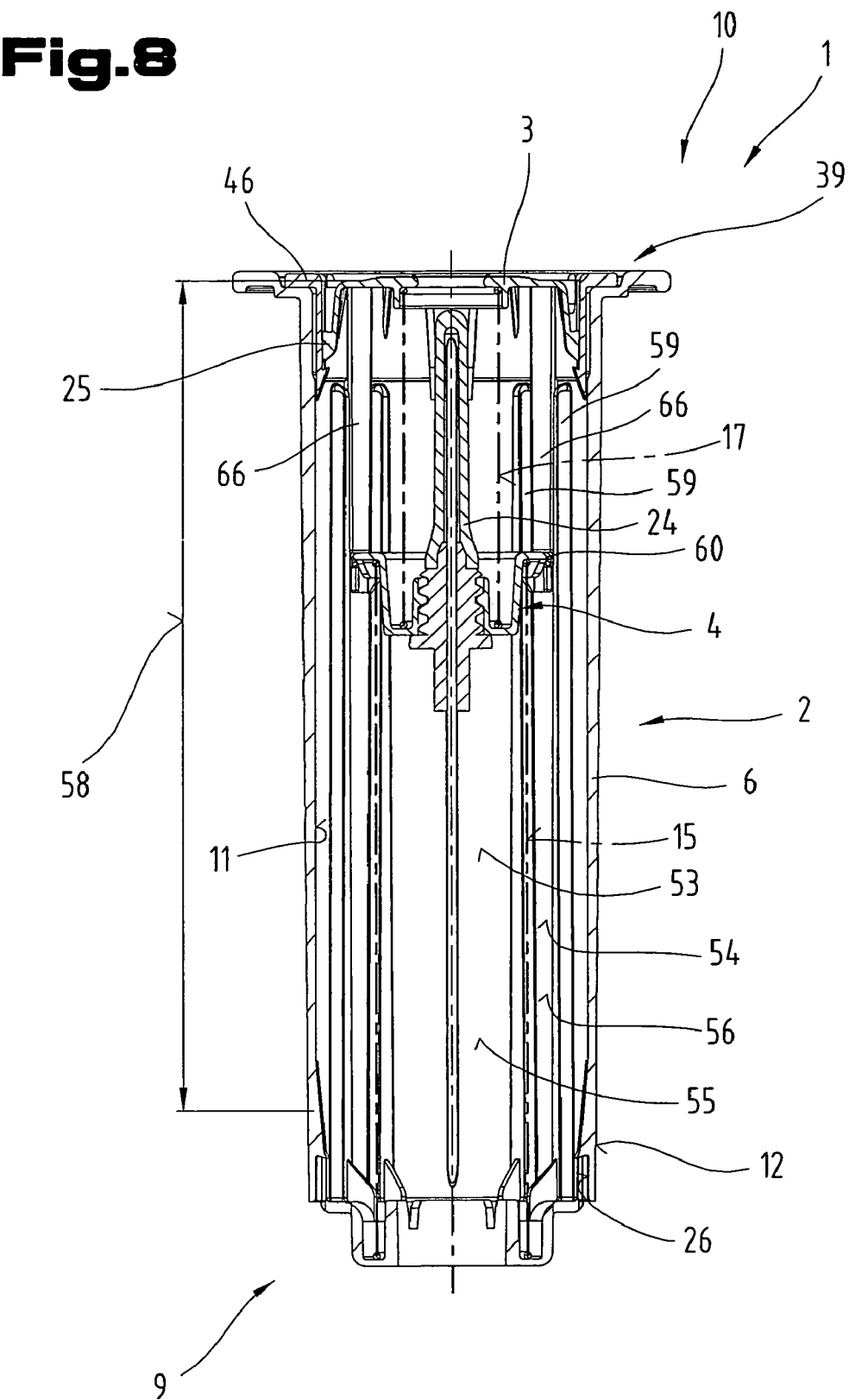
FIG. 8 shows the holding device according to FIG. 7 in the disposal position, in cross section in side view, but rotated by 90° compared to FIG. 7.
Figure 9:
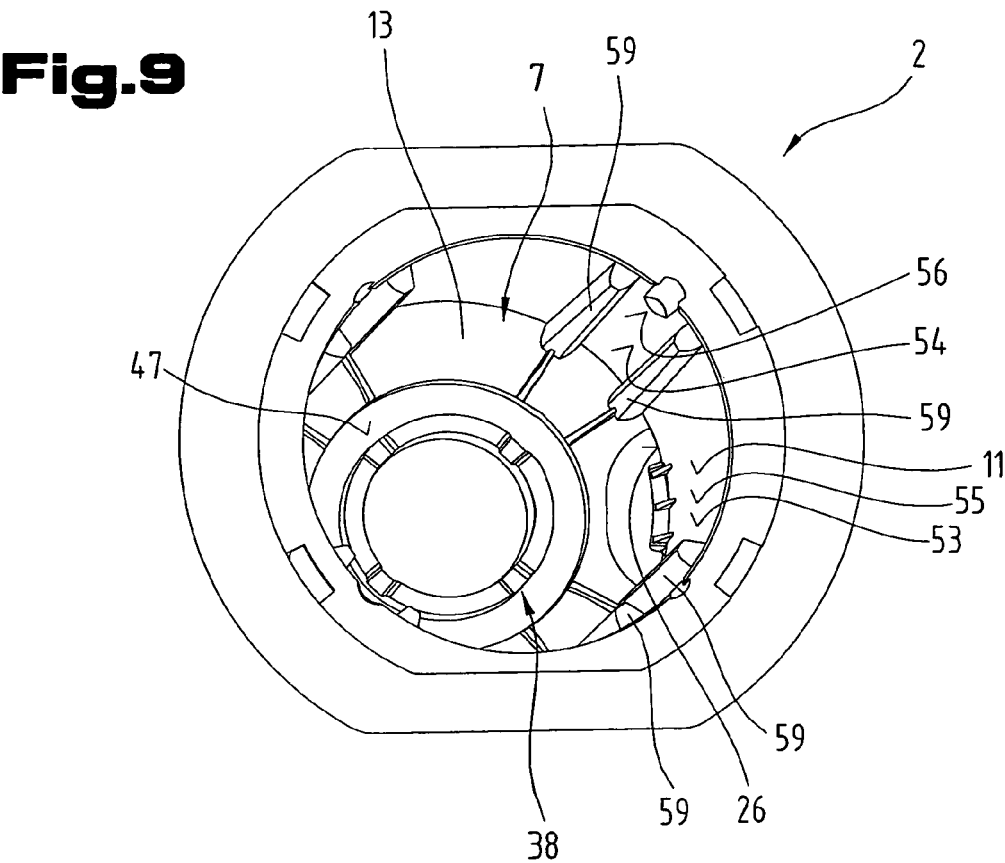
FIG. 9 shows the holding container according to FIGS. 7 and 8 in simplified perspective view.
Figure 10:
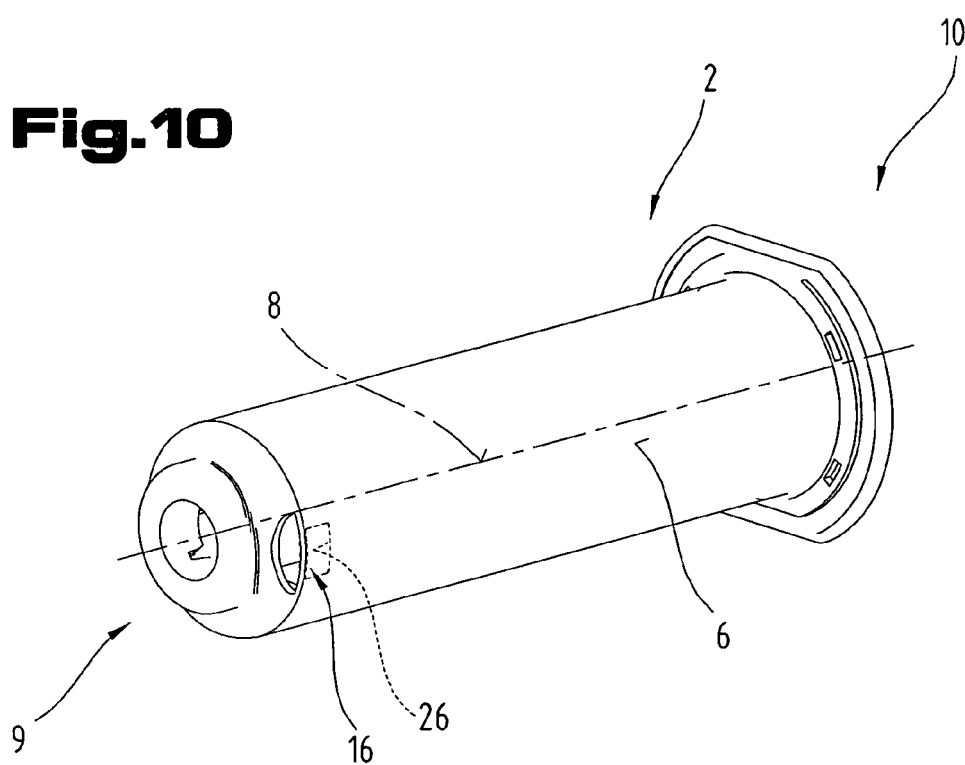
FIG. 10 shows the holding container according to FIG. 9 in a different simplified perspective view.
Figure 13:
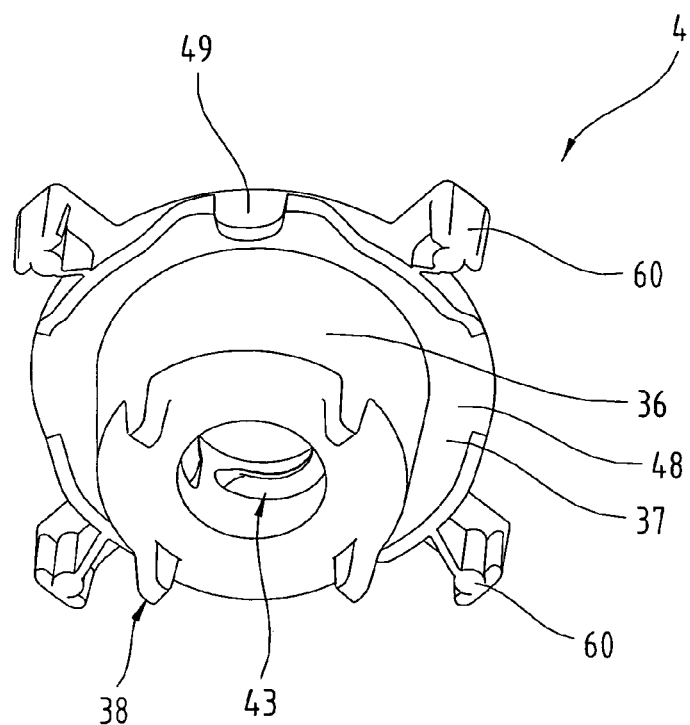
FIG. 13 shows the needle holder according to FIGS. 7 and 8 in simplified perspective view.
Figure 14:
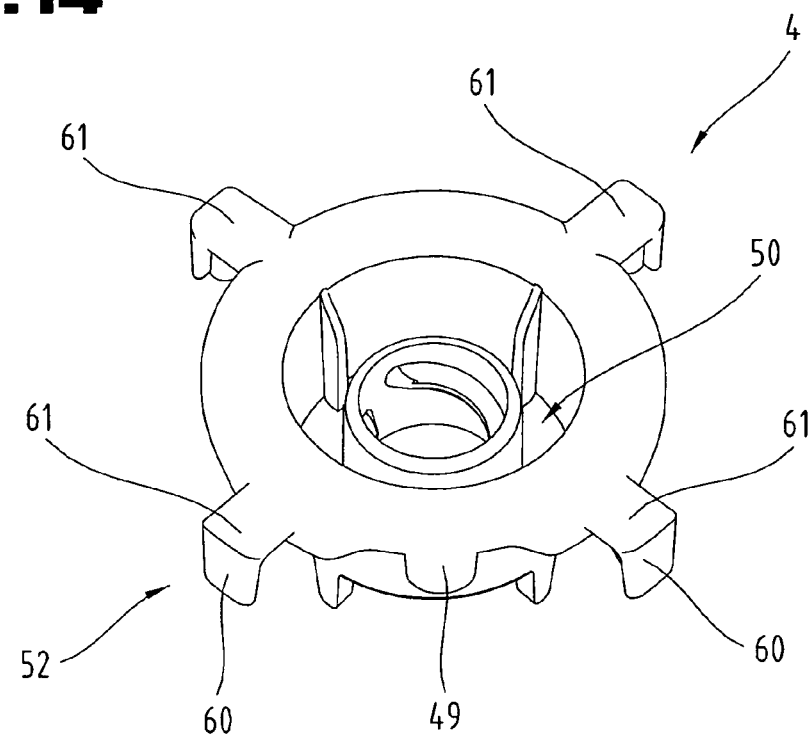
FIG. 14 shows the needle holder according to FIG. 13 in a different simplified perspective view.

As can be seen from the simplified illustration of the holding device 1 in FIGS. 7 and 8, the first adjusting device 15 is arranged between the end wall 13 and the needle holder 4. In order to centre or stabilise the adjusting device 15 in the region of the end wall 10 on the side facing the holding chamber there is a groove-shaped depression 47 in which one end of the adjusting device 15 is inserted. The other end of the adjusting device 15 is supported on at least one support element 37 projecting over the sleeve-shaped supporting body 36 radially outwards. In this embodiment the support element 37 is designed as a support element 48 that passes around the circumference and projects over the supporting body 36. In addition, it is also possible to have at least one first centring element 49 for the first adjusting device 15 arranged in the region of the support element 48 or the support element 37 facing the proximal end 9. By means of the interaction of the supporting body 36 with the centring element or elements 49 the first adjusting device 15 is positioned relative to the needle holder 4.

Furthermore, the centring element 49 can also be used for prior orientation and subsequently for the correct positional insertion of the needle holder 4 into the holding chamber 7. As the thread arrangement 43, as already described in FIGS. 1 to 6, and explained again briefly in the following, has to adopt a definite predetermined position relative to the holding container 2 and the locking device 16 arranged between the latter and the cover element 3 for the alignment of the cannula tip, this predetermined insertion position is important for this procedure. In this way with a single-handed operation of the holding device 1 by a simple releasing of the locking device 16 the end of the cannula 5 located during appropriate use can be removed from the patient by the displacement forces applied by the adjusting devices 15, 17 without having to be held, and thus a change in position of the entire holding device 1 has to occur in relation to the patient. In this way, the removal of the cannula end from the patient is possible in a single-handed operation, for example by the interaction of the thumb and index finger, and the injection site can be covered with a swab by the other free hand. In this way the operating personnel experience a high degree of safety and the risk of injury from unintentional needle sticking and an associated infection is much reduced if not eliminated altogether.

Furthermore, in the centre of the sleeve-shaped supporting body 36 is the thread arrangement 43 for the needle arrangement 14, which is aligned with the threads of the needle arrangement 14 in such a way, that in a completely screwed in position a shorter opening axis of the opening at the tapered cannula tip in the region of the proximal end 9 is aligned roughly parallel to the two opposite locking recesses 26. The thread arrangement 43 for the needle arrangement 14 can be a two-threaded thread, whereby the thread segments are aligned in such as way that with the opposite arrangement and horizontal alignment of the releasable locking device 16 for the cover element 3, a tapering 45 arranged on a cannula tip 44 is provided on an upper side of the cannula 5, as already explained in the description and illustration in the drawing of FIG. 1. Irrespective of this however, of course any other coupling device can be used to connect the needle arrangement 14 and the needle holder 4. At the same time the needle arrangement 14 can also comprise only one cannula 5 with a suitably designed retaining section, whereby the cannula 5 faces the proximal end 9 exclusively and does not project into the holding chamber 7. Thus a syringe needle could also be used.

It can also be see from FIG. 8, that the locking device 16 in the region of the holding container 2 has at least one projection assigned to the locking elements 25 and projecting over the inner surface 11 in the direction of the longitudinal axis 8, whereby said projection forms the end of the locking recess 26. Said locking recess 26 is in the present case only designed to be recessed in the container wall 6 and is closed in the region of the outer surface 12. In this region the container wall only has a very low strength which enables the locking device 16 to be activated. By means of the covered design of the locking recess 26 additional protection from the leaking of fluids to the outside from the holding container 7 is provided. This would otherwise be possible more easily by the displacement of the cannula tip into the holding chamber 7.

The additional adjusting device 17 between the needle holder 4 and the cover element 3 is supported, on the one hand, in the region of the needle holder 4 in the region of the supporting body 36, or if necessary the support element 37 facing the distal end 10, and on the other hand, is supported on the main body 21 of the cover element 3. Preferably, in the region of the needle holder 4 facing the distal end 10, in particular the supporting body 36, in the latter a further tubular depression 50 is formed, into which one end of the additional adjusting device 17 can be inserted. In this way a good centring of the latter can be achieved.

A further centring element 51 for the additional adjusting device 17 can also be arranged on the cover element 3 on the region of the main body 21 facing the proximal end. Said centring element 51 is here in the form of a tubular step on the main body 21, and can serve as an internal or external centring for the spring element, preferably formed by a compression spring made of metal or plastic material.

From an overview of FIGS. 7 to 9 and 17 and 18, it can be seen that between the holding container 2, in particular its container wall 6 and the cover element 3, at least the first guiding arrangement 27 is provided, and between the needle holder 4 and the collecting container 2 a further guiding arrangement 52 is provided. In order to form at least one part of the guide arrangement 27, 52 a partial section 53, 54 of the inner surface 11 of the container wall 6 is designed respectively as a guide track 55, 56. Preferably, the guide tracks 55, 56 or the partial sections 53, 54 are aligned over their longitudinal extension, relative to the longitudinal axis 8, parallel thereto. It is particularly preferable if the partial sections 53, 54 of the inner surface 11 or the entire inner surface 11 are cylindrical in relation to the longitudinal axis 8—i.e. at a constant distance from the longitudinal axis 8. It would also be possible however to design the entire inner surface 11 or only at least one of the partial sections 53, 54 to have a manufacturing-defined tapering. The latter can e.g. be a maximum of 0.5° and is dependent on the selected manufacturing method and the materials used.

As already described above in FIGS. 1 to 6 the first guiding arrangement 27 is designed between the cover element 3 and the holding container 2. The locking device 16 comprises at least one locking element 25 and at least one locking recess 26 interacting therewith in the holding container 2. The locking recess 26 can either be arranged in the container wall 6 or in the region of the end wall 13. In the embodiment shown here on the main body 21 of the cover element 3, several, preferably four, locking elements 25 are provided arranged evenly around the circumference, whereby in the holding container 2 several, preferably two, diametrically opposite locking recesses 26 are arranged or cut out which cooperate with two of the locking elements 25 to form the locking device 16.

It is also possible that the locking element or elements 25 is or are arranged on a holding arm 57 projecting from the main body 21 of the cover element 3 in the direction of the needle holder 4 or the proximal end 9, as can best be seen from FIGS. 11 and 12. In this way the locking elements 25, and if necessary the holding arm or arms 57 are arranged in the region of the outer circumference of the cover element 3. The first guiding arrangement 27 extends at least over the entire displacement path 58 of the cover element 3 between the position of use or its maintenance position in the region of the proximal end 9 and the disposal position or its cover position in the region of the distal end 10. In this way, it is ensured that the cover element 3 during its entire adjustment movement is adjustable continually in the direction of the longitudinal axis 8. The first guiding arrangement 27 is here formed by the bearing or interaction of the locking element or elements 25 arranged on the holding arm 57 on the guide track or tracks 55. It is advantageous in this case, if the locking element or elements 25 bear with the interconnection of the holding arm 57 with a predeterminable or predetermined bearing force radially in the direction of the guide track 55.

If as already described above the partial section 53 of the guide track 55 is aligned parallel to the longitudinal axis 8 over the entire displacement path 58 of the cover element 3 an almost equally high bearing force is achieved.

The additional guiding arrangement 52 between the holding container 2 and the needle holder 4 comprises in the region of the holding container 2 at least one guide element 59 arranged on the inner surface 11 of the latter and projecting in the direction of the longitudinal axis 8, projecting over the inner surface 11, such as e.g. a web, a rib or the like. In order to achieve a straight-line adjustment the guide element or elements 59 is or are aligned in the direction of the longitudinal axis 8. Preferably, two guide elements 59 arranged next to one another, as viewed around the circumference, form a part of the additional guiding arrangement 52 between the holding container 2 and the needle holder 4. In order to achieve a more even and more tilt-free guiding, preferably several guide elements 59 are distributed evenly in pairs around the circumference, and in particular are arranged in the form of a cross relative to one another. As already described above, the additional guiding arrangement 52 comprises at least one further guide track 56, which is arranged between the two adjacent guide elements 59.

As can best be seen from FIGS. 7, 8 and 13 and 14 the additional guiding arrangement 52 in the region of the needle holder 4 comprises at least one guide extension 60 interacting with the guide element or elements 59. The guide extension 60 is hereby designed to be roughly web-shaped and extends in parallel to the longitudinal axis 8. In the embodiment shown here the guide extension or extensions 60 are connected with the interconnection of a support arm 61, illustrated in simplified form, with the support element 37 or support part 48 and connected with the supporting body 36. Preferably, the entire needle holder 4 is made from a one-piece component, in particular by injection moulding.

In the assembled state the guide extension or extensions 60 are arranged in the region of the holding container 2 between the two adjacent guide elements 59, and are guided on the one hand in radial direction by the partial section 54 forming the guide track 56 and viewed in the direction of the longitudinal axis 8, by at least one guiding element, but preferably between the two guide elements 59. The guide extensions 60 and if necessary the support arms 61 are arranged relative to one another on the support element 37 or support element 48 according to the circumferential arrangement of the guide elements 59, preferably distributed evenly around the circumference, in particular in the form of a cross relative to one another.

With an even number of guide tracks 55, 56 arranged on the inner surface the latter are arranged in a cross shape—i.e. at 90° to one another—around the circumference. Furthermore, the guide tracks 55 are arranged offset in relation to the guide tracks 56 by an equal amount around the circumference, whereby an angle of 90° has proved to be preferable. The first guiding arrangement 27 described above, between the cover element 3 and the holding container 2, is formed at least by the locking elements 25 brought to bear on the inner surface 11. To achieve the rotation-fastness of the cover element 3 about the longitudinal axis 8 it is advantageous, if at least one of the guide elements 59 projects into at least one partial cut-out 62 formed in the circumferential region of the cover element 3, or is in engagement with the latter, whereby the partial cut-out 62, viewed in the circumferential region, is arranged in the main body 21 between the locking elements 25 or holding arms 57. This can best be seen in the simplified drawing of FIG. 17.

Figure 15:
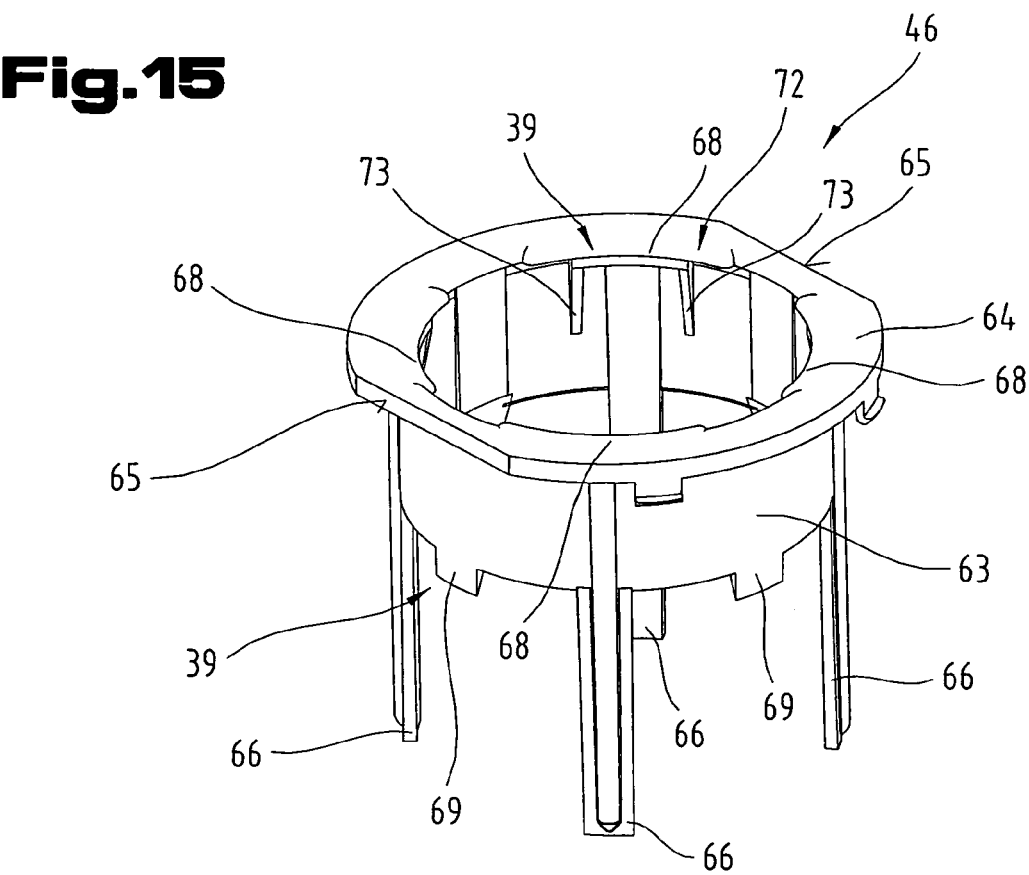
FIG. 15 shows the securing element according to FIGS. 7 and 8 in simplified perspective view.
Figure 16:
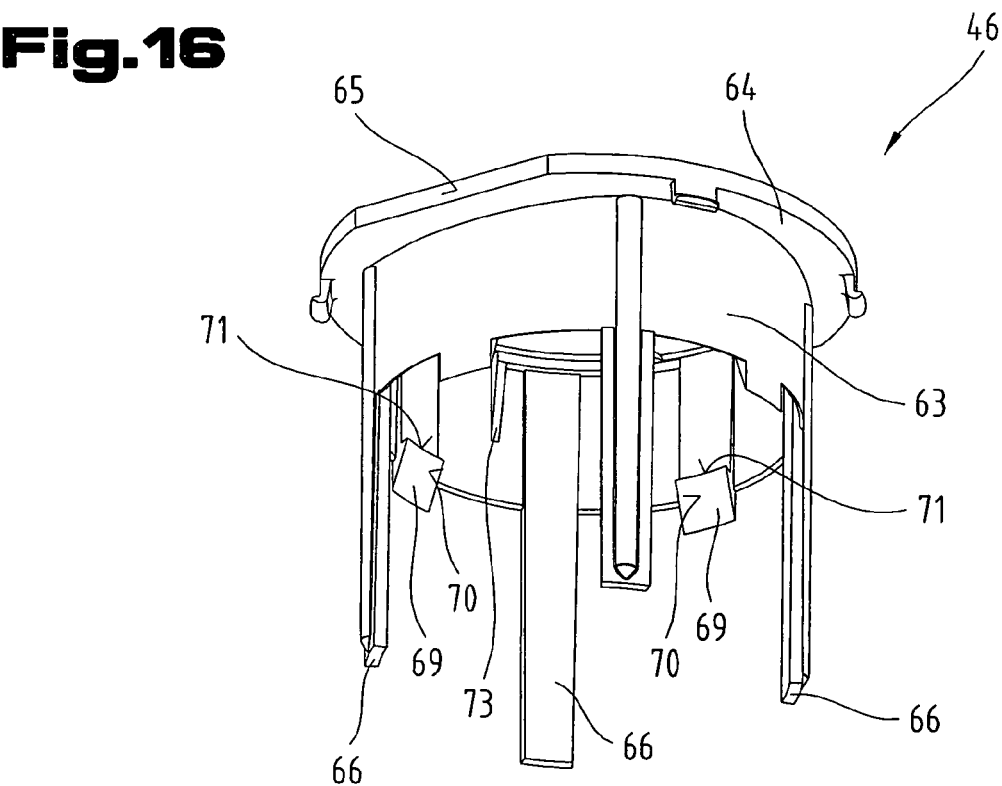
FIG. 16 shows the securing element according to FIG. 15 in a different simplified perspective view.

As described in the introduction to the Figures, in this embodiment in addition in the region of the distal end 10 of the holding container 2, at least one securing element 46 is arranged on the latter, which can best be seem from an overview of FIGS. 15, 16 and 18. Said securing element 46 is designed for subsequent insertion into the holding chamber 7 and held locked on the holding container 2. In the embodiment shown here the securing element 46 comprises a sleeve-shaped support element 63 and flange-shaped step 64 associated therewith, which projects over the support element 63 in the direction pointing away from the longitudinal axis 8. For better positioning it can be advantageous if the flange-shaped step 64 comprises diametrically opposite flattened sections 65, and the latter can be inserted in cooperation with the step 64 into a depression of the holding container 2 arranged in the region of the distal end 10.

On the sleeve-shaped support element 63 at least one positioning element 66 aligned parallel to the longitudinal axis can be arranged which projects over the support element 63 in the direction of the proximal end 9 of the holding container 2. Advantageously several, preferably four, positioning elements 66 are distributed evenly around the circumference, in particular in the form of a cross. This arrangement corresponds in terms of angle to the arrangement of the partial sections 54 of the inner surface 11 of the holding container 2, as can best be seen from FIG. 9. During the assembly the positioning elements 66 project in the direction of the proximal end 9 and are in addition still arranged between the guide elements 59 arranged next to one another in pairs. Said positioning elements 66 project thus into the part section 54 or guide tracks 56 for the guide extensions 60 arranged on the needle holder 4 and delimit a displacement path 67 of the needle holder 4 from the proximal end 9 in the direction of the distal end 10. In this way it is possible for the adjusting device 15 to be provided with correspondingly high preloading force, in order to ensure a secure adjustment of the needle holder 4 and thus of the needle arrangement 14 into the disposal position and to press the needle holder 4 by the stop of the guide extensions 60 against the ends of the positioning elements 66 facing the proximal end 9.

In order to restrict the displacement path 58 of the cover element 3 and thus prevent the exit of the latter out of the holding chamber 7 of the holding container 2, in this embodiment instead of the stop element 42, described in FIGS. 1 to 6, which was arranged directly on the holding container 2, here on the securing element 46 at least one, preferably several, stop elements 68 are arranged around the circumference. Said stop elements 68 project in this embodiment, from the flange-like step 64 in the direction of the longitudinal axis 8, and are thus secure in cooperation with the locking element or elements 41 on the cover element 3, its longitudinal movement from the proximal end 9 in the direction of the distal end.

In order to prevent the cover element 3 from being pressed in from the distal end 10 in the direction of the proximal end 9 in the disposal position, on the securing element 46 at least one, preferably several, retaining elements 69 can be arranged, which in turn form with at least one, preferably several, cooperating further stop elements on the cover element 3, in particular the locking element or elements 25 arranged on the holding arm 57, a part of the locking device 39. The retaining elements 69 are in the installed position of the securing element 46 in the holding container 2 closer to the proximal end 9 and in order to facilitate the intersliding or mutual locking with the allocated locking elements 25 comprise a tapered running surface 70, which is designed to taper from the outer edge of the support element 63 closer to the proximal end 9 and immediately adjacent to the inner surface 11 of the holding container 2 in the direction of the longitudinal axis 8 and the distal end 9. For the mutual locking with the locking element 25 on the retaining element 69 an interacting locking catch 71 is arranged which projects over the tubular support element 63 in the direction of the longitudinal axis 8 and with the running surface 70 forms the locking catch 71.

The locking elements 25, preferably two diametrically opposite ones, on the one hand form the locking device 16 with the locking recess 26 in the position of use in the region of the proximal end 9, and in the region of the distal end 10 in cooperation with retaining elements 69 form a portion of the locking device 39. In the region of the locking device 39 for a better securing of the cover element 3 the locking elements 25 distributed evenly around the circumference act together with the retaining elements 69. In the present embodiment four locking elements 25 and retaining elements 69 are provided distributed evenly around the circumference.

Of course, it is also possible to provide any number of locking elements 25, locking recesses 26, retaining elements 69, stop elements 68 and locking elements 41. This depends on the size, design and the purpose of the holding device 1, and can be selected freely according to the requirements made of the holding device 1.

At the same time, it is also possible, as already described in FIGS. 1 to 6, for the cover element 3 in the region of the longitudinal axis 8 to comprise an opening 22 for guiding through a portion of the cannula 5, whereby in addition in the region of the opening 22, a fluid suctioning or collecting component 23 can be arranged.

The same is also true for the anti-rotational means 38 arranged between the needle holder 4 and the holding container 2. The latter is used when the needle holder 4 is located in the position of use, which on inserting the needle arrangement 14 prevents a relative pivoting or rotation about the longitudinal axis 8 between the needle holder 4 and the holding container 2. In the embodiments described in FIGS. 7 to 17, as can best be seen from an overview of FIGS. 9 and 13, a portion of the anti-rotational means 38 in the region of the end wall 13 of the collecting container 2 is formed by groove or web-shaped depressions and in the region of the needle holder 4 by locking projections projecting over the supporting body 36. In this way in the position of use of the needle holder 4 the locking projections are in engagement with the groove-shaped or web-shaped depressions.

The anti-rotational means 38 can of course also be formed by any other arrangement or design of components in engagement with one another in the position of use, as already described and shown in FIGS. 1 to 6. In the drawing of FIG. 18 the needle holder 4 comprises opposite flattened sections, which can cooperate with correspondingly designed fitting surfaces.

As can be seen from an overview of FIGS. 9, 12, 15, 16 and 18, the cover element 3 during its longitudinal movement from the position of use to the disposal position in the region of the holding container 2 is secured by the partial cut-out 62 arranged on the circumferential region in interaction with guide elements 59 from rotation about the longitudinal axis 8. In the region of the securing elements 46 in particular in the region of its support element 63, no such guide elements 59 are provided in the region of the inner surface 11 of the holding container 2, whereby rotation of the cover element 3 about a specific angle about the longitudinal axis 8 is possible, whereby the locking element or elements 25 can be brought by pivoting or rotation out of engagement with the retaining elements 69, and thus the cover element 3 can be readjusted and pushed in the direction of the proximal end 9 into the holding chamber 7. In this way a stick injury from the end of the cannula 5 arranged in the holding chamber 7 would be possible.

In order to prevent the possibly undesired relative rotation of the cover element 3 relative to the holding container 2 in this embodiment between the latter or between the securing element 46 and the cover element 3 there is one, preferably several, anti-rotational means 72. In the region of the cover element 3 the anti-rotational means 72 is in the form of partial cut-out or cut-outs 62 in the circumferential region of the cover element 3. In the region of the holding container 2 or the securing element 46 the anti-rotational means 72 is formed for example by webs 72 arranged distributed around the circumference, which are arranged in the direction of the longitudinal axis 8 in extension to the guide elements 59 on the inside of the support element 63. In this way also in this position of the cover element 3 is definitely secured and held in position relative to the holding container 2 or the securing element 46 arranged therein both in the direction of the longitudinal axis 8 and about the longitudinal axis 8. Unintentional rotational and any associated injury and resulting infection is thus almost completely eliminated.

For form's sake it should be pointed out that for a better understanding of the structure of the holding device the latter and its components have been illustrated partly untrue to scale and/or enlarged and/or reduced in size.

The objective forming the basis of independent solutions according to the invention can be taken from the description.

Most of all, the individual designs shown in the FIGS. 1 to 6; 7 to 17; 18 can form the subject matter of independent solutions according to the invention. The objectives and solutions relating thereto can be taken from the detailed descriptions of said Figures.

LIST OF REFERENCE NUMBERS

1 Holding device
2 Holding container
3 Cover element
4 Needle holder
5 Cannula
6 Container wall
7 Holding chamber
8 Longitudinal axis
9 Proximal end
10 Distal end
11 Inner surface
12 Outer surface
13 End wall
14 Needle arrangement
15 Adjusting device
16 Locking device
17 Adjusting device
18 Spring element
19 Spring element
20 Plane
21 Main body
22 Opening
23 Component
24 Protective sleeve
25 Locking element
26 Locking recess
27 Guiding arrangement
28 Guiding groove
29 Guiding extension
30 Diameter
31 Diameter
32 Opening
33 Cross sectional dimension
34 Cross sectional dimension
35 Holding chamber
36 Support body
37 Support element
38 Anti-rotational means
39 Locking device
40 Retaining element
41 Locking element
42 Stop element
43 Thread arrangement
44 Cannula tip
45 Tapering
46 Securing element
47 Depression
48 Support element
49 Centring element
50 Depression
51 Centring element
52 Guiding arrangement
53 Partial section
54 Partial section
55 Guide track
56 Guide track
57 Holding arm
58 Displacement path
59 Guide element
60 Guide extension
61 Support arm
62 Partial cut-out
63 Support element
64 Step
65 Flattened section
66 Positioning element
67 Displacement
68 Stop element
69 Retaining element
70 Running surface
71 Locking catch

The invention claimed is:

1. Holding device (1) with a holding container (2) for a holding vessel, wherein the holding container (2) surrounds a holding chamber (7) with a container wall (6), and in the direction of a longitudinal axis (8) comprises a proximal and a distal end (9, 10) spaced apart from one another, whereby the container wall (6) is delimited by an inner surface (11) facing the holding chamber (7) and an outer surface (12) facing away therefrom, with a needle holder (4) for a needle arrangement (14) which can be secured thereon, whereby the needle holder (4) in the holding chamber (7) of the holding container (2) is designed to be displaceable relative to the holding container from a position of use in the region of the proximal end (9) to a disposal position in the direction of the distal end (10), with a first adjusting device (15) for the needle holder (4) for the displacement from the position use into the disposal position, with a cover element (3) for the needle arrangement (14) securable to the needle holder (4) in the disposal position of the needle holder (4) and with a releasable locking device (16), wherein the cover element (3) is formed by a disc-shaped main body (21) aligned in a plane (20) perpendicular to the longitudinal axis (8), whereby the cover element (3) in the position of use of the needle holder (4) is arranged adjacent thereto on the side pointing away from the proximal end (9) in the holding chamber (7), and in that the releasable locking device (16) is arranged between the cover element (3) and the holding container (2), with which the cover element (3) in the position of use of the needle holder (4) is held relative to the holding container (2), and wherein between the needle holder (4) and the cover element (3) an additional adjusting device (17) is arranged formed by an elastically deformable spring element (19), whereby on releasing the locking device (16) the cover element (3) is displaced relative to the needle holder (4) in the direction of the longitudinal axis (8) by the additional adjusting device (17) in the direction of the distal end (10) of the holding container (2).

2. Holding device according to claim 1, wherein the first adjusting device (15) is in the form of a compression spring.

3. Holding device according to claim 1, wherein the additional adjusting device (17) is designed to expand conically from the needle holder (4) up to the cover element (3).

4. Holding device according to claim 1, wherein the first and the additional adjusting device (15, 17) are in the form of a one-piece component.

5. Holding device according to claim 1, wherein the disc-shaped main body (21) of the cover element (3) has an external diameter (30) in the plane (20) perpendicular to the longitudinal axis (8), which corresponds approximately to an inner diameter (31) of the holding chamber (7) in the same plane (20).

6. Holding device according to claim 1, wherein the cover element (3) in the region of the longitudinal axis (8) has an opening (22) for feeding through a portion of the cannula (5).

7. Holding device according to claim 6, wherein in the region of the opening (22) a component (23) is arranged for suctioning or absorbing liquid.

8. Holding device according to claim 1, wherein the locking device (16) comprises at least two diametrically opposite locking elements (25) and locking recesses (26) cooperating therewith.

9. Holding device according to claim 8, wherein the locking elements (25) are arranged on the disc-shaped main body (21) of the cover element (3).

10. Holding device according to claim 1, wherein on the main body (21) of the cover element (3), several, locking elements (25) are arranged distributed evenly around the circumference and in the holding container (2) several, diametrically opposite locking recesses (26) are arranged to form the locking device (16).

11. Holding device according to claim 8, wherein the locking recesses (26) are arranged in the container wall (6) of the holding container (2).

12. Holding device according to claim 8, wherein the locking recesses (26) penetrate the container wall (6) of the holding container (2).

13. Holding device according to claim 8, wherein the locking elements (25) project in radial direction, from the inner surface (11) to the outer surface (12) of the container wall (6), only partially into the locking recesses (26).

14. Holding device according to claim 8, wherein the locking elements (25) are spring-connected to the disc-shaped main body (21) of the cover element (3).

15. Holding device according to claim 8, wherein the locking elements (25) are arranged on a holding arm (57) projecting from the main body (21) of the cover element (3) in the direction of the needle holder (4) or the proximal end (9).

16. Holding device according to claim 8, wherein the locking elements (25) are arranged in the region of the outer circumference of the cover element (3).

17. Holding device according to claim 1, wherein on the region of the main body (21) facing the proximal end (9) at least one first centering element (51) for the additional adjusting device (17) is arranged.

18. Holding device according to claim 1, wherein between the cover element (3) and the inner surface (11) of the container wall (6) at least one first guiding arrangement (27) is provided, which is aligned in the direction of the longitudinal axis (8) of the holding container (2).

19. Holding device according to claim 18, wherein the guiding arrangement (27) extends at least over the entire displacement path (58) of the cover element (3) between its maintenance position in the region of the proximal end (9) and its cover position in the region of the distal end (10).

20. Holding device according to claim 18, wherein the first guiding arrangement (27) is formed by at least one guiding groove (28) indented in the container wall (6) and running in the direction of the longitudinal axis (8) and at least one guiding extension (29) on the cover element (3) engaging with the guiding groove (28).

21. Holding device according to claim 20, wherein several guiding grooves (28) are arranged evenly distributed around the circumference of the holding container (2).

22. Holding device according to claim 20, wherein a groove base of the guiding groove (28) over its longitudinal extension relative to the longitudinal axis (8) runs parallel to the the longitudinal axis.

23. Holding device according to claim 1, wherein the diametrically opposite locking devices (16) viewed in the direction of the longitudinal axis (8) are arranged around the circumference of the holding container (2) symmetrically between the guiding grooves (28).

24. Holding device according to claim 1, wherein between the holding container (2) and the cover element (3) a further guiding arrangement (52) is provided.

25. Holding device according to claim 1, wherein in order to form at least one part of a guiding arrangement (27, 52) a partial section (53, 54) of the inner surface (11) of the container wall (6) is designed as a guide track (55, 56) and is aligned over its longitudinal extension relative to the longitudinal axis (8) in parallel to the the longitudinal axis.

26. Holding device according to claim 25, wherein the partial section (53, 54) of the inner surface (11) or the inner surface (11) is designed to be cylindrical relative to the longitudinal axis (8).

27. Holding device according to claim 18, wherein the first guiding arrangement (27) is formed by the bearing or cooperation of the locking element (25) on the guide track (55) arranged on the holding arm (57).

28. Holding device according to claim 27, wherein the locking element or elements (25) lie with a predeterminable bearing force aligned radially in the direction of the guide track (55).

29. Holding device according to claim 28, wherein the bearing force is almost equal over the entire displacement path (58) of the cover element (3).

30. Holding device according to claim 24, wherein the additional guiding arrangement (52) in the region of the holding container (2) comprises at least one guide element (59), arranged on the inner surface (11) thereof and projecting in the direction of the longitudinal axis (8) and projecting over the inner surface (11).

31. Holding device according to claim 30, wherein the guide element or elements (59) is or are aligned in the direction of the longitudinal axis (8).

32. Holding device according to claim 30, wherein two guide elements (59) arranged next to one another around the circumference form a portion of the additional guiding arrangement (52).

33. Holding device according to claim 32, wherein several guide elements (59) are provided, distributed evenly in pairs around the circumference.

34. Holding device according to claim 24, wherein the additional guiding arrangement (52) comprises at least one further guide track (56) which is arranged between the two adjacently arranged guide elements (59).

35. Holding device according to claim 24, wherein the additional guiding arrangement (52) in the region of the needle holder (4) comprises at least one guide extension (60) cooperating with the guide element or elements (59).

36. Holding device according to claim 35, wherein the guide extension or extensions (60) is or are arranged respectively between the two adjacent guide elements (59).

37. Holding device according to claim 1, wherein the first and the additional guide tracks (55, 56) arranged in the form of a cross relative to one another are offset relative to one another in circumferential direction by 90°.

38. Holding device according to claim 1, wherein at least one guide element (59) projects into at least one partial section (62) formed in the circumferential region of the cover element (3) or is in engagement with the cover element.

39. Holding device according to claim 1, wherein the container wall (6) in the plane (20) aligned perpendicular to the longitudinal axis (8) has a circular cross section, and an external diameter (30) of the disc-shaped main body (21) corresponds approximately to an inner diameter (31) of the holding chamber (7) in this plane.

40. Holding device according to claim 1, wherein the holding container (2) is designed to be open in the region of the distal end (10) and closed in the region of the proximal end (9) partially by an end wall (13).

41. Holding device according to claim 40, wherein the end wall (13) has an opening (32) in the region of the longitudinal axis (8) which corresponds in its inner cross sectional dimension (33) approximately to an outer cross sectional dimension (34) of the needle holder (4).

42. Holding device according to claim 40, wherein in the end wall (13) there is a holding chamber (35) for the first adjusting device (15) or the one-piece component formed by the adjusting devices (15, 17).

43. Holding device according to claim 1, wherein the needle holder (4) is formed by a roughly sleeve-shaped supporting body (36).

44. Holding device according to claim 43, wherein on the sleeve-shaped supporting body (36) in the plane (20) aligned perpendicular to the longitudinal axis (8) at least one support element (37) projecting radially outwards over the carrier body is arranged.

45. Holding device according to claim 44, wherein on the support element (37) the adjusting devices (15, 17) are supported at the end regions facing one another.

46. Holding device according to claim 45, wherein at least one of the end regions is secured firmly to the support element (37).

47. Holding device according to claim 44, wherein the support element (37) in a one piece design of the adjusting device (15, 17) is arranged in a transition region thereof and is secured thereto.

48. Holding device according to claim 44, wherein the support element (37) is designed as a support element (48) running around the circumference and projecting over the supporting body (36) radially.

49. Holding device according to claim 43, wherein on the region of the support element (48) facing the proximal end (9) at least one first centering element (49) is arranged.

50. Holding device according to claim 43, wherein in the region of the needle holder (4) facing the distal end (10) a tubular depression (49) is arranged in the sleeve-shaped supporting body (36).

51. Holding device according to claim 43, wherein in the sleeve-shaped supporting body (36) a thread arrangement (43) is provided for the needle arrangement (14).

52. Holding device according to claim 51, wherein the thread arrangement (43) is aligned in such a way, that with an opposite arrangement and horizontal alignment of the releasable locking device (16) for the cover element (3) a tapering (45) on a cannula tip (44) is provided on an upper side of the cannula (5).

53. Holding device according to claim 1, wherein between the needle holder (4) and the holding container (2) an anti-rotational means (38) is arranged, which in the position of use of the needle holder (4) is in engagement and prevents a relative pivoting or rotation between the needle holder about the longitudinal axis (8).

54. Holding device according to claim 1, wherein the cover element (3) with the needle holder (4) located in the disposal position is secured in the region of the distal end (10) relative to the holding container (2) in its longitudinal movement in the direction of the longitudinal axis (8) by means of a locking device (39).

55. Holding device according to claim 54, wherein the locking device (39) comprises at least one retaining element (40) arranged on the holding container (2) and facing the distal end (10) and at least one locking element (41) cooperating therewith on the cover element (3).

56. Holding device according to claim 54, wherein the retaining element (40) is formed by a spring element of the container wall (6), which is designed at least over a portion of its longitudinal extension in the direction of the longitudinal axis (8) to project over the inner surface (11) in the direction of the longitudinal axis (8).

57. Holding device according to claim 54, wherein the retaining element or elements (40) are arranged in the region of the guiding arrangement (27).

58. Holding device according to 53, wherein the locking device (39) comprises at least one stop element (42) for the cover element (3) arranged on the holding container (2) and facing the distal end (10).

59. Holding device according to claim 58, wherein the stop element or elements (42) are arranged in the region of the guiding arrangement (27).

60. Holding device according to claim 1, wherein in the region of the distal end (10) of the holding container (2) at least one securing element (46) is arranged on the holding container.

61. Holding device according to claim 60, wherein the securing element (46) is inserted into the holding container (7) and is locked onto the holding container (2).

62. Holding device according to claim 60, wherein the securing element (46) comprises a sleeve-shaped support element (63) and a flangeshaped step (64) connected therewith, which projects over the support element (63) in the direction away from the longitudinal axis (8).

63. Holding device according to claim 60, wherein on the sleeve-shaped support element (63) at least one positioning element (66) aligned in parallel direction to the longitudinal axis (8) is arranged, which projects over the support element (63) in the direction of the proximal end (9).

64. Holding device according to claim 63, wherein several positioning elements (66) are provided distributed evenly around the circumference.

65. Holding device according to claim 1, wherein the positioning element (66) projects into the additional guide track (56) arranged between the two adjacent guide elements (59).

66. Holding device according to claim 1, wherein in the disposal position the guide extension (60) of the needle holder (4) is supported at the end of the positioning element (66) facing the proximal end (9).

67. Holding device according to claim 1, wherein the locking device (39) comprises at least one retaining element (69) arranged on the securing element (46) and closer to the proximal end (9) and at least one locking element (25) on the cover element (3) interacting therewith.

68. Holding device according to claim 1, wherein the locking device (39) also comprises at least one stop element (68) for the cover element (3) arranged on the securing element (46) and facing the distal end (10).

69. Holding device according to claim 1, wherein in the disposal position an anti-rotational means (72) is in engagement between the securing element (46) and the cover element (3).

* * * * *

UNITED STATES PATENT AND TRADEMARK OFFICE
CERTIFICATE OF CORRECTION

PATENT NO. : 7,521,022 B2
APPLICATION NO. : 10/530301
DATED : April 21, 2009
INVENTOR(S) : Franz Konrad It is certified that error appears in the above-identified patent and that said Letters Patent is hereby corrected as shown below:

In particular, in Column 23, line 19 (Line 2 in Claim 10), after the word "several" please delete: "," .

In Column 23, line 21 (Line 4 in Claim 10), after the word "several" please delete: ",".

Signed and Sealed this

Thirtieth Day of June, 2009

JOHN DOLL
*Acting Director of the United States Patent and Trademark Office*